US008592209B2

(12) United States Patent
Khurgel et al.

(10) Patent No.: US 8,592,209 B2
(45) Date of Patent: *Nov. 26, 2013

(54) METHODS OF PREPARING AND CHARACTERIZING MESENCHYMAL STEM CELL AGGREGATES AND USES THEREOF

(75) Inventors: Moshe Khurgel, Charlottesville, VA (US); Adam J. Katz, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 995 days.

This patent is subject to a terminal disclaimer.

(21) Appl. No.: 12/162,523

(22) PCT Filed: Jan. 30, 2007

(86) PCT No.: PCT/US2007/002572
§ 371 (c)(1),
(2), (4) Date: Jul. 29, 2008

(87) PCT Pub. No.: WO2007/089798
PCT Pub. Date: Aug. 9, 2007

(65) Prior Publication Data
US 2009/0304643 A1    Dec. 10, 2009

Related U.S. Application Data

(60) Provisional application No. 60/763,333, filed on Jan. 30, 2006.

(51) Int. Cl.
*C12N 5/02* (2006.01)
(52) U.S. Cl.
USPC .......................................... 435/395; 435/366
(58) Field of Classification Search
USPC .................. 435/366, 395; 424/93.7
See application file for complete search history.

(56) References Cited

U.S. PATENT DOCUMENTS

| | | | |
|---|---|---|---|
| 5,486,359 A | 1/1996 | Caplan et al. | |
| 5,591,625 A | 1/1997 | Gerson et al. | |
| 5,827,735 A | 10/1998 | Young et al. | |
| 5,827,740 A | 10/1998 | Pittenger | |
| 5,906,934 A | 5/1999 | Grande et al. | |
| 5,908,784 A | 6/1999 | Johnstone et al. | |
| 6,200,606 B1 | 3/2001 | Peterson et al. | |
| 6,429,013 B1 | 8/2002 | Halvorsen et al. | |
| 7,887,843 B2 | 2/2011 | Libera et al. | |
| 7,932,084 B2 * | 4/2011 | Katz et al. | 435/325 |
| 2001/0033834 A1 * | 10/2001 | Wilkison et al. | 424/93.7 |
| 2002/0076400 A1 | 6/2002 | Katz et al. | |
| 2006/0045872 A1 | 3/2006 | Miguel et al. | |
| 2006/0147430 A1 | 7/2006 | Sayre et al. | |
| 2007/0110729 A1 | 5/2007 | Kang et al. | |
| 2007/0116676 A1 | 5/2007 | Kida et al. | |
| 2009/0304643 A1 | 12/2009 | Khurgel et al. | |
| 2010/0098739 A1 | 4/2010 | Katz et al. | |
| 2010/0111897 A1 | 5/2010 | Katz et al. | |

FOREIGN PATENT DOCUMENTS

| | | |
|---|---|---|
| KR | 20050012208 | 1/2005 |
| WO | WO 0053795 | 9/2000 |
| WO | WO 03022988 | 3/2003 |
| WO | WO-03084468 A2 | 10/2003 |
| WO | WO-2004022988 A1 | 3/2004 |
| WO | WO-2005045011 A1 | 5/2005 |
| WO | WO-2005114178 A1 | 12/2005 |
| WO | WO-2006032054 A2 | 3/2006 |
| WO | WO-2007019107 A2 | 2/2007 |
| WO | WO 2007030652 | 3/2007 |
| WO | WO-2007089798 A1 | 8/2007 |
| WO | WO-2007089798 A2 | 8/2007 |
| WO | WO-2007089798 A3 | 8/2007 |
| WO | WO-2008060374 A2 | 5/2008 |
| WO | WO-2008060374 A3 | 5/2008 |
| WO | WO-2008064034 A2 | 5/2008 |

OTHER PUBLICATIONS

Kruse et al., Pluripotency of adult stem cells derived from human and rat pancreas, 2004, Applied Physics A, 79: 1617-1624.*
G. Erickson, et al., "Chondrogenic Potential of Adipose Tissue-Derived Stomal Cells in Vitro and in Vivo", Biochemical and Biophysical Research Communication, 2002, 290, 763-769.
S. Gronthos, et al., "Surface Protein Characterization of Human Adipose Tissue-Derived Stromal Cells", Journal of Cellular Physiology, 2001, 189, 54-63.
Y. Halvorsen, et al., "Thiazolidinediones and Glucocorticoids Synergistically Induce Differentiation of Human Adipose Tissue Stomal Cells: Biochemical, Cellular, and Molecular Analysis", Metabolism, Apr. 2001, 50:4, 407-413.
Y. Halvorsen, et al., "Extracellular Matrix Mineralization and Osteblast Gene Expression by Human Adipose Tissue-Derived Stromal Cells", Tissue Engineering, 2001, 7:6, 729-741.
J. Harp, et al., "Differential Expression of Signal Transducers and Activators of Transcription during Human Adipogenesis", Biochemical and Biophysical Research Communications, 2001, 281, 907-912.
R. Saladin, et al., "Differential Regulation of Peroxisome Proliferator Activated Receptor γ1 (PPARγ1) and PPARγ2 Messenger RNA Expression in the Early Stages of Adipogenesis1", Cell Growth & Differentiation, Jan. 1999, 10, 43-48.
A. Sen, et al., "Adipogenic Potential of Human Adipose Derived Stromal Cells from Multiple Donors is Heterogeneous", Journal of Cellular Biochemistry, 2001, 81, 312-319.
"European Application Serial No. 07762669.5, Search Report mailed Apr. 14, 2009", 6 pgs.
"European Application Serial No. 07762669.5, Office Action mailed Apr. 21, 2010", 4 Pgs.

(Continued)

*Primary Examiner* — Jon P Weber
*Assistant Examiner* — Robert Yamasaki
(74) *Attorney, Agent, or Firm* — Schwegman, Lundberg & Woessner, P.A.

(57) ABSTRACT

The invention provides compositions and methods for preparing and characterizing multipotential mesenchymal stem cell aggregates. The invention further provides methods for using stem cell aggregates of the invention.

16 Claims, 20 Drawing Sheets

(56) References Cited

OTHER PUBLICATIONS

"European Application Serial No. 07762669.5, Office Action Response Filed Oct. 27, 2010", 59 pgs.

"International Application Serial No. PCT/US07/02572, International Search Report mailed Dec. 28, 2007", 4 pgs.

Howson, K. M, et al., "The postnatal rat aorta contains pericyte progenitor cells that form spheroidal colonies in suspension culture", Am J Physiol Cell Physiol., 289(6), (Dec. 2005), C1396-C1407 pgs.

Oshima, Y, et al., "Fate of transplanted bone-marrow-derived mesenchymal cells during osteochondral repair using transgenic rats to simulate autologous transplantation.", Osteoarthritis Cartilage, 12(10), (Oct. 2004), 811-7 pgs.

Oshima, Y., et al., "Behavior of transplanted bone marrow-derived GFP mesenchymal cells in osteochondral defect as a simulation of autologous transplantation.", J Histochem Cytochem., 53(2), (Feb. 2005), 207-216 pgs.

"International Application Serial No. PCT/US2007/002572, International Preliminary Report on Patentability mailed Aug. 5, 2008", 9 pgs.

"International Application Serial No. PCT/US2007/002572, Written Opinion mailed Dec. 28, 2007", 8 pgs.

"European Application Serial No. 07762669.5, Office Action mailed Aug. 8, 2011", 5 pgs.

"U.S. Appl. No. 12/444,412 Response File Dec. 5, 2011 to Non final Office Action mailed Jun. 3, 2011", 10 pgs.

"U.S. Appl. No. 12/444,412, Non Final Office Action mailed Jun. 3, 2011", 16 pgs.

"U.S. Appl. No. 12/444,412, Preliminary Amendment mailed Apr. 6, 2009", 3 pgs.

"U.S. Appl. No. 12/444,412, Preliminary Amendment mailed Jun. 11, 2009", 3 pgs.

"U.S. Appl. No. 12/444,412, Response filed Mar. 21, 2011 to Restriction Requirement mailed Feb. 18, 2011", 8 pgs.

"U.S. Appl. No. 12/444,412, Restriction Requirement mailed Feb. 18, 2011", 9 pgs.

"U.S. Appl. No. 12/580,419, Non Final Office Action mailed Sep. 1, 2011", 8 pgs.

"International Application Serial No. PCT/US2007/021432, International Preliminary Report on Patentability mailed Apr. 7, 2009", 6 pgs.

"International Application Serial No. PCT/US2007/021432, Written Opinion mailed Sep. 12, 2008", 5 pgs.

Burris, T. P, et al., "A novel method for analysis of nuclear receptor function at natural promoters: peroxisome proliferator-activated receptor gamma agonist actions on aP2 gene expression detected using branched DNA messenger RNA quantitation.", Mol Endocrinol., 13(3), (Mar. 1999), 410-7.

Campos, L. S, "Neurospheres: insights into neural stem cell biology", J Neurosci Res., 78(6), (Dec. 15, 2004), 761-9.

Conley, B. J, et al., "Derivation, propagation and differentiation of human embryonic stem cells", Int J Biochem Cell Biol., 36(4), (Apr. 2004), 555-67.

Dontu, G., et al., "Survival of mammary stem cells in suspension culture: implications for stem cell biology and neoplasia.", J Mammary Gland Biol Neoplasia, 10(1), (Jan. 2005), 75-86.

Fuchs, E., et al., "Socializing with the neighbors: stem cells and their niche", Cell, 116(6), (Mar. 19, 2004), 769-78.

Gimble, J. M, et al., "The function of adipocytes in the bone marrow stroma", New Biol., 2(4), (Apr. 1990), 304-12.

Gorio, A., et al., "Fate of autologous dermal stem cells transplanted into the spinal cord after traumatic injury (TSCI).", Neuroscience, 125(1), (2004), 179-89.

Hauner, H., et al., "Promoting effect of glucocorticoids on the differentiation of human adipocyte precursor cells cultured in a chemically defined medium.", J Clin Invest., 84(5), (Nov. 1989), 1663-70.

Kindler, V., "Postnatal stem cell survival: does the niche, a rare harbor where to resist the ebb tide of differentiation, also provide lineage-specific instructions?", J Leukoc Biol., 78(4), (Oct. 2005), 836-44.

Rodbell, M., "Metabolism of isolated fat cells. II. The similar effects of phospholipase C (*Clostridium perfringens* alpha toxin) and of insulin on glucose and amino acid metabolism", J Biol Chem., 241(1), (Jan. 10, 1966), 130-9.

Stafford, Kristine M, et al., "Stem Cell Therapy for neurologi disorders: Tehrapeutic potential of Adipose-Derived Stem Cells", Current Drug Targets, 6, (2005), 57-62.

Yamashita, Y. M, et al., "Signaling in stem cell niches: lessons from the *Drosophila* germline", J Cell Sci., 118(Pt 4), (Feb. 15, 2005), 665-72.

Zhou, L., et al., "Analysis of the pattern of gene expression during human adipogenesis by DNA microarray", Biotechnology Techniques, 13(8), (Aug. 1999), 513-517.

"U.S. Appl. No. 12/444,412, Advisory Action mailed Mar. 19, 2012", 3 pgs.

"U.S. Appl. No. 12/444,412 , Response filed Mar. 7, 2012 to Final Office Action mailed Feb. 8, 2012", 9 pgs.

"U.S. Appl. No. 12/444,412, Advisory Action mailed Mar. 9, 2012", 3 pgs.

"U.S. Appl. No. 12/444,412, Non Final Office Action mailed Feb. 8, 2012", 17 pgs.

"U.S. Appl. No. 12/444,412, Response filed Aug. 8, 2012 to Final Office Action mailed Feb. 8, 2012", 9 pgs.

"Japanese Application Serial No. 2008-553314, Office Action mailed Jun. 5, 2012", With English Translation, 6 pgs.

Johnstone, Brian, et al., "In vitro chondrogenesis of bone marrow-derived mesenchymal progenitor cells", Exp Cell Res., 238(1), (Jan. 10, 1998), 265-72.

Kang, Kyung Sun, et al., "Multipotent Stem Cells Derived From Human Adipose Tissue and Cellular Therapeutic Agents Comprising the Same filed Nov. 16, 2005", (2007).

Kelm, Jens M, et al., "Method for generation of homogeneous multicellular tumor spheroids applicable to a wide variety of cell types", Biotechnol. Bioeng., 83(2), (2003), 173-180.

Khurgel, Moshe, et al., "Methods of Preparing and Characterizing Mesenchymal Stem Cell Aggregates and Uses Thereof filed Jan. 30, 2006", (2009).

* cited by examiner

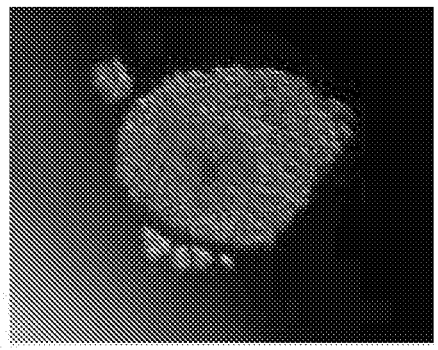 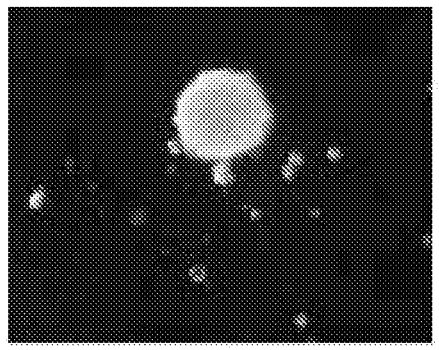
FIG. 1A    FIG. 1B
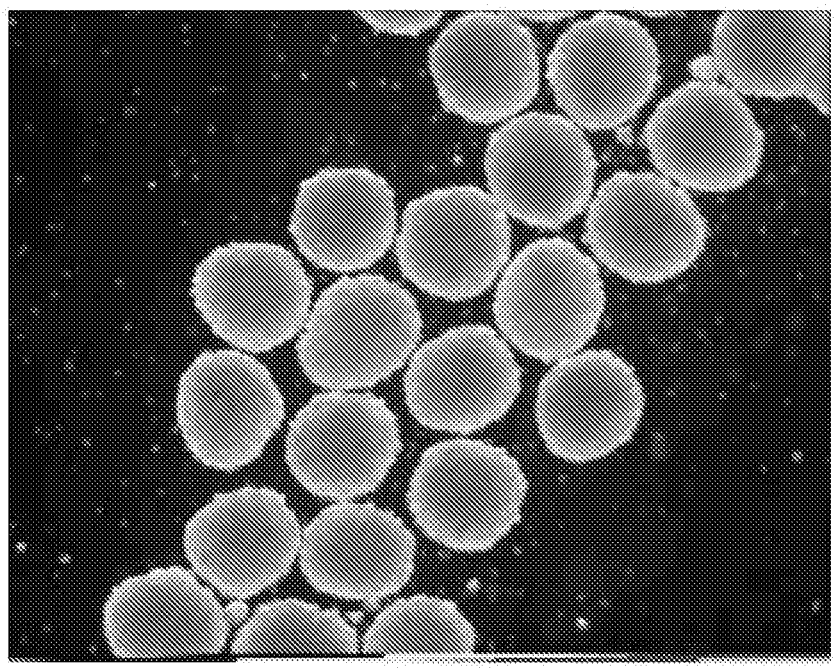
FIG. 2

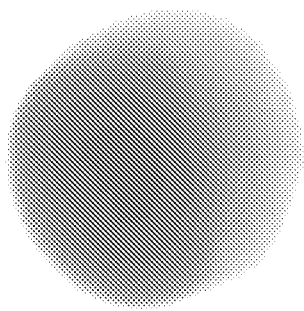
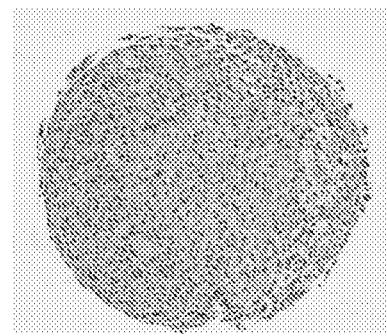
FIG. 19A          FIG. 19B
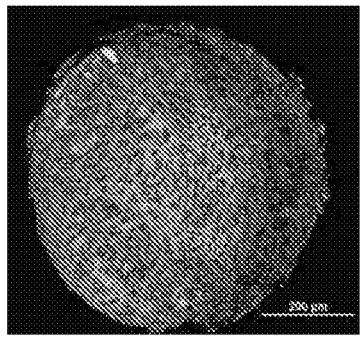
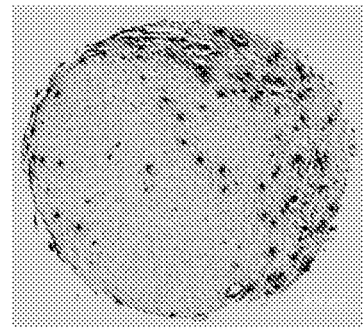
FIG. 19C          FIG. 19D

METHODS OF PREPARING AND CHARACTERIZING MESENCHYMAL STEM CELL AGGREGATES AND USES THEREOF

STATEMENT REGARDING FEDERALLY SPONSORED RESEARCH OR DEVELOPMENT

This invention was made with United States Government support under Grant No. HL72141, awarded by the National Institutes of Health. The United States Government has certain rights in the invention.

CROSS REFERENCE TO RELATED APPLICATIONS

This application is a national stage filing of International Application No. PCT/US2007/002572, filed on Jan. 30, 2007, which claims priority under 35 U.S.C. §119(e) to U.S. Provisional Application Ser. No. 60/763,333 filed Jan. 30, 2006, the disclosures of which are incorporated by reference in their entirety herein.

BACKGROUND

Mesenchymal stem cells are stem cells that can be isolated from a variety of tissues such as bone marrow, adipose tissue, dermis/skin, etc. These cells are the subject of intense scientific research and scrutiny and are thought to represent a cornerstone for potentially revolutionary paradigms of regenerative therapies of the future.

Mesenchymal stem cells in general, and adipose stem cells in particular, hold great promise for future clinical therapies which enhance the body's natural ability to heal itself. One hurdle common to the use of these potential therapies is the current practice of using fetal bovine serum or other animal sera in the culture media of cells intended for use in humans. The undefined and variable nature of animal sera, as well as the associated risk of introducing xenobiotic pathogens and triggering severe allergic responses in some subjects, presents a technical problem presently unresolved in the field.

In recent years, the identification of mesenchymal stem cells, chiefly obtained from bone marrow, has led to advances in tissue regrowth and differentiation. Such cells are pluripotent cells found in bone marrow and periosteum, and they are capable of differentiating into various mesenchymal or connective tissues. For example, such bone-marrow derived stem cells can be induced to develop into myocytes upon exposure to agents such as 5-azacytidine (Wakitani et al., Muscle Nerve, 18 (12), 1417-26 (1995)). It has been suggested that such cells are useful for repair of tissues such as cartilage, fat, and bone (see, e.g., U.S. Pat. Nos. 5,908,784, 5,906,934, 5,827,740, 5,827,735), and that they also have applications through genetic modification (see, e.g., U.S. Pat. No. 5,591,625). While the identification of such cells has led to advances in tissue regrowth and differentiation, the use of such cells is hampered by several technical hurdles. One drawback to the use of such cells is that they are very rare (representing as few as 1/2,000,000 cells), making any process for obtaining and isolating them difficult and costly. Of course, bone marrow harvest is universally painful to the donor. Moreover, such cells are difficult to culture without inducing differentiation, unless specifically screened sera lots are used, adding further cost and labor to the use of such stem cells.

The presence of adult multipotent "stem" cells has been demonstrated in a large number of tissues, for example the bone marrow, blood, liver, muscle, the nervous system, and in adipose tissue. Adult "stem" cells, which in theory are capable of infinite self-renewal, have great cell plasticity, i.e., the ability to differentiate into tissues other than those for which it was believed they were destined. The properties of said cells, which are similar to those of embryonic stem cells (ES), open up considerable therapeutic perspectives especially as their use does not pose the problems of compatibility and ethics, encountered with ES cells.

Adipose tissue plays an important and overlooked role in the normal development and physiology of humans and other mammalian species. Many different kinds of fat exist. The most common type is white adipose tissue, located under the skin (subcutaneous fat), within the abdominal cavity (visceral fat) and around the reproductive organs (gonadal fat). Less common in the adult human is brown adipose tissue, which plays an important role in generating heat during the neonatal period; this type of fat is located between the shoulder blades (interscapular), around the major vessels and heart (periaortic and pericardial), and above the kidney (suprarenal).

As women mature, they develop increased amounts of mammary adipose tissue. The mammary fat pad serves as an energy source during periods of lactation. Indeed, reproductive capacity and maturation are closely linked to the adipose tissue stores of the individual. Puberty in women and men correlates closely with the production and release of leptin, an adipose tissue derived hormone, and to body fat composition. Other adipose tissue sites play a structural role in the body. For example, the mechanical fat pads in the soles of the feet provide a cushion against the impact of walking. Loss of this fat depot leads to progressive musculoskeletal damage and impaired mobility. Bone marrow fat cells are present in bone marrow to provide energy to developing blood cells within the marrow.

Bone marrow adipocytes are different than adipocytes present in adipose tissue, differing in morphology, physiology, biochemistry as well as their response to various stimulators such as insulin. Adipocytes present in bone marrow stroma may function to: 1) regulate the volume of hemodynamically active marrow; 2) serve as a reservoir for lipids needed in marrow cell proliferation, and 3) may be developmentally related to other cell lineages such as osteoblasts. White adipose tissue (i.e. body fat) in contrast, is involved in lipid metabolism and energy homeostasis (Gimble, "The Function of Adipocytes in the Bone Marrow Stroma", The New Biologist 2(4), 1990, pp. 304-312).

The vast majority of research related to various stem cell populations has centered on their behavior and therapeutic potential as adherent cell cultures and/or single cell suspensions that are either mixed in nature, or clonally derived. However, a consensus is evolving, supported by promising evidence, that stem cells most likely exist in vivo within the context of a supportive niche, or microenvironment.

As reviewed in several recent papers, emerging data suggest that "it is the combination of the intrinsic characteristics of stem cells and their microenvironment that shapes their properties and defines their potential" (Fuchs et al., Cell, 116:769-778, 2004). In essence, the specific cellular environment, or niche, is composed of a diverse, heterogeneous collection of cells (in addition to, or including the stem cell constituents) that create/provide a milieu of soluble and matrix factors. These factors help to direct and control the homeostasis of the stem cell reservoir, including cell growth, differentiation, and renewal (Kindler, J. Leukocyte Biol., 78:836-844, 2005; Fuchs et al., Cell, 116:769-778, 2004). And while it is currently thought that the majority of stem cells are dormant/quiescent in the $G_0$ phase of the cell cycle when a tissue/niche is in equilibrium, it is also believed that loss of, or damage to a tissue/niche provides a powerful stimulus to the stem cell reservoir to re-establish equilibrium (i.e., repair; regenerate) by renewal (expansion) and/or differentiation. This capacity likely involves asymmetric cell division and possibly some degree of dedifferentiation, all of which is thought to be governed by the niche micromilieu.

Given the above background, it becomes clear that the 'creation' of ex vivo stem cell niche models would be highly useful and valuable for the study of stem cell biology, as well as for potential therapeutic applications. Researchers have described and characterized in vitro 'niches' for embryonic stem cells (embryoid bodies) and neural stem cells (neurospheres)—which both involve suspension (i.e., non-adherent) culture of said cells in multicellular aggregates. However, no such 'system' has been described for mesenchymal stem/stromal cells, particularly adipose-derived cells. Such cells are traditionally cultured as adherent monolayers, and this is likely due to the difficulty in culturing these cells in suspension, as they are extremely adherent, even to surfaces that are supposedly unfavorable to cell culture/adherence.

There is a long felt need in the art for methods to prepare, characterize, and manipulate multicellular aggregates of mesenchymal stem cells, particularly adipose tissue-derived cells, and to provide for alternative, and/or enhanced regenerative technologies. The present invention satisfies this need.

BRIEF SUMMARY OF THE INVENTION

The present invention provides methods and compositions to grow and to differentiate adipose stem/stromal cell populations. The present invention further provides methods and compositions to manipulate and engineer clusters of such cells.

The present application discloses multiple ways to culture human adipose-derived stem/stromal cells (ASCs) in suspension culture such that they: 1) form and organize into 3-dimensional multicellular aggregates (which can also be described as spheres, clusters, blastemas, networks, etc.) that survive for prolonged time in culture (suspension or adherent) with or without serum, or other xenogeneic proteins; 2) can repeatedly 'spawn' adherent cells that grow to confluence (i.e. extensive self-renewal capability); 3) can differentiate into multilineage phenotypes, and 4) can morph (grow, elongate, polarize) in response to different environmental conditions, such as various media or trauma. In addition, these 3-dimensional aggregates can be formed as cellular chimeras by using 2 or more different cell types, such as ASCs and keratinocytes, or ASCs and hematopoietic stem cells (HSCs). These 3-dimensional cell aggregates are referred to as blastemas herein. A blastema is defined as a cluster of cells that are competent to initiate, facilitate, and/or direct the regeneration of a damaged or ablated structure/tissue. Throughout this document, these blastemas are further described and interchangeably referred to as Self-Organizing Mesenchymal Blastemas (SOM-Bs), adipose stem/stromal cell blastemas (ASCBs), chimeric blastemas (CBs), and/or ASC-mesenchymal blastemas (ASC-MBs).

The present invention encompasses the fabrication, culture, maintenance, and/or manipulation of human adipose-derived stem/stromal cells in suspension (non-adherent) conditions such that they organize into novel 3-dimensional, multicellular, dynamic, self-sufficient structures. The results disclosed in the present application suggest that these ex vivo structures are comparable to a quiescent stem cell niche (micro-environment) of/for ASCs and which can maintain the cells in an undifferentiated and/or dedifferentiated state (as they might exist in vivo). Upon the appropriate signals and/or conditions such as exposure to growth factors and/or tissue injury, the cells in those niches have the capacity to replicate, differentiate, and/or undergo migration, polarization and/or other morphogenic/developmental behaviors. The presently disclosed data further suggest that ASCs prepared in or derived from this niche environment have enhanced developmental plasticity (as compared to cells grown as adherent monolayer cultures using standard techniques), and therefore enhanced regenerative therapeutic potential. SOM-Bs represent a novel delivery system/strategy for regenerative medicine applications with the potential for enhancing the engraftment and survival of transplanted cells, as well as enhancing their incorporation, migration and differentiation within the host site. Because ASCs represent a particularly practical and appealing source of cells for the translation of regenerative therapies to the clinic, this discovery has significant implications for the use of ASCs in research, diagnostics, and therapeutics.

The invention described herein pertains to the culture of ASCs in such a manner that they form 3-dimensional, multicellular aggregates that behave like a stem cell population in a supportive niche/microenvironment.

In one embodiment, the invention provides a method of culturing ASCs such that they organize into a three-dimensional multicellular structure. In one aspect, the ASCs form aggregates in culture, called SOM-Bs. In one aspect, the aggregates are non-adherent, i.e., are in suspension. In one aspect, the culture medium is serum-free. In one aspect, the medium comprises about 0.5% serum. In one aspect, the medium used is AR8 or AR9. In one aspect, the SOM-Bs can be propagated in culture. In one aspect, the SOM-Bs comprise cells capable of proliferating. In one aspect, the SOM-Bs are capable of movement/migration. In one aspect, SOM-Bs comprise cells capable of differentiating into at least one cell type. In one aspect, SOM-Bs comprise cells capable of differentiating into various cell types, including, but not limited to, adipocytes, osteoblasts and chondrocytes, depending on the environmental conditions or stimuli present. In one aspect, at least one SOM-B can fuse with at least one other SOM-B. In one aspect, the ASCs are human ASCs.

In one embodiment, cells in SOM-Bs secrete factors capable of modulating the activity and function of cells adjacent to the SOM-B or near to the SOM-B. In one aspect, the factors are growth factors. In another aspect, the factors are differentiation factors. In yet another aspect, the factors are angiogenic factors.

In one embodiment, cells in SOM-Bs secrete extracellular matrix proteins.

In one embodiment, SOM-Bs may be formed which further comprise cells other than ASCs, such that a chimera is formed.

In one embodiment, SOM-Bs are propagated in culture. In one aspect, the culture is suspension culture.

In one embodiment, SOM-Bs are administered to a subject in need thereof. In one aspect, the SOM-Bs can be co-administered with drugs or other agents or compounds. Such compounds include, but are not limited to, peptides, ribozymes, nucleic acids, oligonucleotides, antisense oligonucleotides, aptamers, phylomers, polymers, biodegradable scaffolds, and siRNA.

In one embodiment, ASCs are at least partially purified prior to being cultured. In one aspect, cellular markers are used to purify the cells. In one aspect, the cellular markers are selected from the group consisting of CD34, NG2, ABCG2, CXCR4, CD271, CD140b, CD105, ALDH and HLA-1.

Various aspects and embodiments of the invention are described in further detail below.

BRIEF SUMMARY OF THE DRAWINGS

Some of the original photographs are color photographs. Therefore, when reference is made to a color other than black, gray, or white, it should be noted that it will appear as a gray color in the black and white photographs submitted herewith.

FIG. 1, comprising left (1A) and right (1B) panels, represents images of photomicrographs depicting Formation of Self-Organizing Mesenchoid Bodies (SOM-Bs) from ASCs in inverted droplet.

FIG. 2 represents an image of a photomicrograph depicting the technique which allows consistent formation of cell spheres/SOMBs of uniform size.

FIG. 3, comprising

FIG. 5, comprising

FIG. 10, comprising

FIG. 12A (upper left panel) represents two smaller SOMBs which have just made contact. FIG. 12B represents the beginning of fusion. Following fusion SOMBs continue to dynamically reorganize, as is evidenced by shape changes and fusion of DiI$^+$ "cores" (12C and 12D). FIGS. 12C and 12D (lower panels) demonstrate the spontaneous self-organization that occurs when multiple SOMBs fuse.

FIG. 14, comprising

FIG. 19, comprising FIGS. 19A to 19D (four panels), represents images of micrographs depicting directional growth of SOM-Bs (ASC-MBs) in suspension culture. (19A) Light micrograph of an ASC-MB grown in suspension culture in serum-free medium, with early evidence of polarization and directional growth. (19B) H&E histology of the same ASC-MB demonstrates defined nuclei throughout a background of ASC-derived extracellular matrix. (19C) Fluorescent micrograph of the same section in (19B) demonstrates the more intense, cell and matrix-dense 'core' relative to the growing 'apical' edge (toward the right of the MB). (19D) Reveals a light micrograph of a section from the same ASC-MB that has been immunohistochemically stained for BrdU (brown nuclei). The ASC-MB was grown in serum-free medium for 8 days, and pulsed with BrdU for 24 hours prior to fixation and staining. The observed staining pattern correlates perfectly with the proliferative activity observed at the non-fluorescent pole.

FIG. 20, comprising

FIG. 27, comprising

DETAILED DESCRIPTION OF THE INVENTION

Abbreviations and Acronyms

Figure 3A:
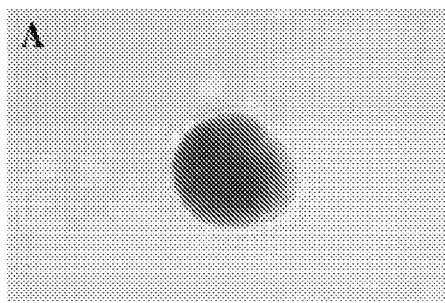
FIGS. 3A-D, represents images of photomicrographs demonstrating that SOM-Bs grow dramatically, mostly in a polarized fashion, in chemically-defined media (AR series). Labeling of ASCs with DiI prior to SOMB formation (FIGS. 3A and 3C) allows for visualization of growth and polarization (star in 3C marks the original cell population).
Figure 3B:
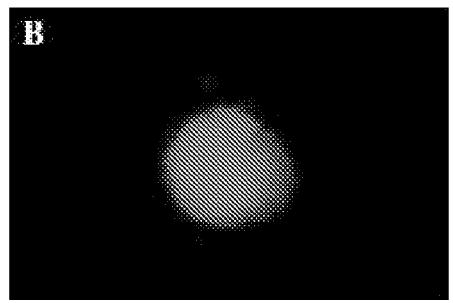
Figure 3C:
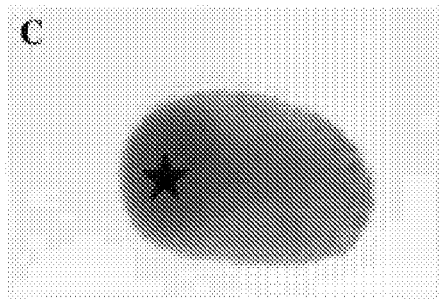
Figure 3D:
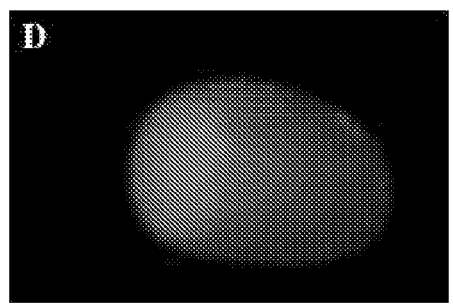

ASC—adipose tissue-derived stem cell
ASCB—adipose stem/stromal cell blastema
ASC-MB—ASC-mesenchymal blastema
CB—chimeric blastema
DMEM—Dulbecco's modified Eagle's medium
ES—embryonic stem cell
FACS—fluorescent activated cell sorting
FBS—fetal bovine serum.
HSC—hematopoietic stem cell
MB—mesenchoid body
SOM-B—Self-Organizing Mesenchymal Blastema (also referred to as "self-organizing mesenchoid bodies" herein)
ULA—ultra low attachment tissue culture plate

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

"Adipose-derived stem cells", also referred to as "adipose-derived stromal cells" herein, refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, more preferably, the adipose tissue is human. A convenient source of adipose tissue is from liposuction surgery, however, the source of adipose tissue or the method of isolation of adipose tissue is not critical to the invention.

The term "adult" as used herein, is meant to refer to any non-embryonic or non-juvenile subject. For example the term "adult adipose tissue stem cell," refers to an adipose stem cell, other than that obtained from an embryo or juvenile subject.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

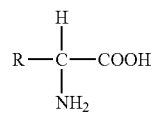

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values; unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "autologous", as used herein, refers to something that occurs naturally and normally in a certain type of tissue or in a specific structure of the body. In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "blastema", as used herein, encompasses inter alia, the primordial cellular mass from which an organ, tissue or part is formed as well as a cluster of cells competent to initiate and/or facilitate the regeneration of a damaged or ablated structure.

The term "biocompatible," as used herein, refers to a material that does not elicit a substantial detrimental response in the host.

The terms "cell" and "cell line," as used herein, may be used interchangeably. All of these terms also include their progeny, which are any and all subsequent generations. It is understood that all progeny may not be identical due to deliberate or inadvertent mutations.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

A "compound," as used herein, refers to any type of substance or agent that is commonly considered a drug, or a candidate for use as a drug, combinations, and mixtures of the above, as well as polypeptides and antibodies of the invention.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The term "delivery vehicle" refers to any kind of device or material which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect.

The term "feeder cells" as used herein refers to cells of one type that are co-cultured with cells of a second type, to provide an environment in which the cells of the second type can be maintained, and perhaps proliferate. The feeder cells can be from a different species than the cells they are supporting. Feeder cells can be non-lethally irradiated or treated to prevent their proliferation prior to being co-cultured to ensure to that they do not proliferate and mingle with the cells which they are feeding. The terms, "feeder cells", "feeders," and "feeder layers" are used interchangeably herein.

As used herein, a "functional" molecule is a molecule in a form in which it exhibits a property or activity by which it is characterized.

A "fragment" or "segment" is a portion of an amino acid sequence, comprising at least one amino acid, or a portion of a nucleic acid sequence comprising at least one nucleotide. The terms "fragment" and "segment" are used interchangeably herein.

"Graft" refers to any free (unattached) cell, tissue, or organ for transplantation.

"Allograft" or "allogeneic" refers to a transplanted cell, tissue, or organ derived from a different animal of the same species.

"Xenograft" or "xenogeneic" refers to a transplanted cell, tissue, or organ derived from an animal of a different species.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, means to suppress or block an activity or function such that it is lower relative to a control value. The inhibition can be via direct or indirect mechanisms. In one aspect, the activity is suppressed or blocked by at least 10% compared to a control value, more preferably by at least 25%, and even more preferably by at least 50%.

The term "inhibitor" as used herein, refers to any compound or agent, the application of which results in the inhibition of a process or function of interest, including, but not limited to, differentiation and activity. Inhibition can be inferred if there is a reduction in the activity or function of interest.

The term "injury" refers to any physical damage to the body caused by violence, accident, trauma, or fracture, etc.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

Used interchangeably herein are the terms: 1) "isolate" and "select"; and 2) "detect" and "identify".

The term "isolated," when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays which distinguish cell types.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, *Antibodies, A Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "low adherence, ultra low adherence, or non-adherence surface for cell attachment" refers to the ability of a surface to support attachment of cells. The term "non-adherence surface for cell attachment" means that the surface supports little if any cell attachment.

The term "modulate", as used herein, refers to changing the level of an activity, function, or process. The term "modulate" encompasses both inhibiting and stimulating an activity, function, or process.

The terms "multicellular aggregate", "multicellular sphere", "blastema", and "multicellular structure" are used interchangeably herein.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

"Plurality" means at least two.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

The term "propagate" means to reproduce or to generate.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups; for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

As used herein, the term "solid support" when used in reference to a substrate forming a linkage with a compound, relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "solid support suitable for maintaining cells in a tissue culture environment" is meant any surface such as a tissue culture dish or plate, or even a cover, where medium containing cells can be added, and that support can be placed into a suitable environment such as a tissue culture incubator for maintaining or growing the cells. This should of course be a solid support that is either sterile or capable of being sterilized. The support does not need to be one suitable for cell attachment.

The term "solid support is a low adherence, ultralow adherence, or non-adherence support for cell culture purposes" refers to a vehicle such as a bacteriological plate or a tissue culture dish or plate which has not been treated or prepared to enhance the ability of mammalian cells to adhere to the surface. It could include, for example, a dish where a layer of agar has been added to prevent cells from attaching. It is known to those of ordinary skill in the art that bacteriological plates are not treated to enhance attachment of mammalian cells because bacteriological plates are generally used with agar, where bacteria are suspended in the agar and grow in the agar.

The term "spawn", as used herein, refers to the ability of the multicellular spheres of cells disclosed herein (SOMBs) to generate adherent cells (i.e., progeny) with the ability, inter alia, to grow to confluence.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In one aspect, the activity or differentiation is stimulated by at least 10% compared to a control value, more preferably by at least 25%, and even more preferably by at least 50%. The term "stimulator" as used herein, refers to any compound or agent, the application of which results in the stimulation of a process or function of interest, including, but not limited to, ASC cell production, differentiation, and activity, as well as that of ASC progeny.

A "subject" of analysis, diagnosis, or treatment is an animal. Such animals include mammals, preferably a human.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "substituent" as used in the phrase "other cells which are not substituents of the at least one self-organizing blastema" refers to substituent cells of the blastema. Therefore, a cell which is not a substituent of a self-organizing blastema can be a cell that is adjacent to the blastema and need not be a cell derived from a self-organizing blastema.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The use of the phrase "tissue culture dish or plate" refers to any type of vessel which can be used to plate cells for growth or differentiation.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

Embodiments

The present invention provides methods and compositions for growing adipose stem/stromal cells and forming the cell clusters described herein. In one embodiment, serum-free culture medium is provided. In one aspect, the medium is AR8. In another embodiment, the invention provides culture medium and techniques for enhancing or stimulating proliferation of adipose tissue cells. In one aspect, the methods of enriching such cells includes methods of inducing differentiation of the precursor cells.

The present invention provides methods for identifying and characterizing populations of adipose stem/stromal cells and derivatives thereof. In one aspect, the invention provides antibodies directed against the cells of the invention.

Adult human subcutaneous adipose tissue represents a stromal/stem cell source that can be harvested routinely with minimal risk or discomfort to the patient. Evidence suggests that adipose-derived stromal cells are capable of differentiation along multiple lineage pathways. Adipose tissue is readily accessible and abundant in many individuals. Obesity is a condition of epidemic proportions in the United States, where over 50% of adults exceed the recommended BMI based on their height and weight.

US 2002/0076400 and WO 00/53795 describe the production of multipotent cell populations from human adipose tissue. Said cell populations can be differentiated into adipocytes, osteoblasts, chondrocytes, and myocytes. The publications indicate that some of the cells they can be maintained in culture in vitro for at least 15 cell transfers without losing their multipotent character.

U.S. Pat. No. 6,800,480 describes methods and materials for growing primate-derived primordial stem cells in a feeder cell-free culture system.

It is well documented that adipocytes are a replenishable cell population. Even after surgical removal by liposuction or other procedures, it is common to see a recurrence of adipocytes in an individual over time. This suggests that adipose tissue contains stromal stem cells that are capable of self-renewal.

Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there are up to $8.6 \times 10^4$ stromal cells per gram of adipose tissue (Sen et al., 2001, Journal of Cellular Biochemistry 81:312-319). Ex vivo expansion over 2 to 4 weeks yields up to 500 million stromal cells from 0.5 kilograms of adipose tissue. These cells can be used immediately or cryopreserved for future autologous or allogeneic applications.

Adipose derived stromal cells also express a number of adhesion and surface proteins. These include, but are not limited to, cell surface markers such as CD9; CD29 (integrin beta 1); CD44 (hyaluronate receptor); CD49d,e (integrin alpha 4, 5); CD54 (ICAM1); CD55 (decay accelerating factor); CD105 (endoglin); CD106 (VCAM-1); CD166 (AL-CAM) and HLA-ABC (Class I histocompatibility antigen); and cytokines such as interleukins 6, 7, 8, 11; macrophage-colony stimulating factor; GM-colony stimulating factor; granulocyte-colony stimulating factor; leukemia inhibitory factor; stem cell factor and bone morphogenetic protein. Many of these proteins have the potential to serve a hematopoietic supportive function and the majority of them are shared in common by bone marrow stromal cells.

The adipose tissue-derived stem/stromal cells useful in the methods of invention are isolated by a variety of methods known to those skilled in the art such as described in WO 00/53795 to the University of Pittsburgh et al. In a preferred method, adipose tissue is isolated from a mammalian subject, preferably a human subject. In one aspect, a source of adipose tissue is omental adipose. In another aspect, it is subcutaneous adipose. In humans, the adipose is typically isolated by liposuction. If the cells of the invention are to be transplanted into a human subject, it is preferable that the adipose tissue be isolated from that same subject to provide for an autologous transplant. Alternatively, the transplanted cells are allogeneic.

Many techniques are known to those of ordinary skill in the art which can be used to help isolate, culture, induce differentiation, and to characterize the cells of the invention (Gorio et al., 2004, Neuroscience, 125:179-189; Yamashita et al., 2005, J. Cell Sci., 118:665-672; Conley et al., 2004, The International Journal of Biochemistry and Cell Biology, 36:555-567; Kindler, 2005, Journal of Leukocyte Biology, 78:836-844; Fuchs et al., 2004, Cell, 116:769-778; Campos, 2004, Journal of Neuroscience Research, 78:761-769; Dontu et al., 2005, Journal of Mammary Gland Biology and Neoplasia, 10:75-86).

In one aspect, the invention provides methods for determining the optimal number of cells required for forming various sized SOM-Bs. In one aspect, the SOM-B is considered an "effective" SOM-B, where effective means capable of displaying the desired characteristics of growth, polarization, differentiation capacity, etc. The invention also provides methods for determining where cell growth is occurring in the SOM-B, what kind of matrix is being produced, where the matrix is being produced, and how much matrix is being produced. Methods are known in the art for determining the above-described properties, as well as for measuring such characteristics as cell growth rate, etc.

Methods are also known in the art which can be used to determine how frequently SOM-Bs can spawn adherent cells and the characteristics of those spawned cells, such as growth rate, ability to reach confluency, developmental plasticity, etc. Methods are also available which can be used to determine frequency of SOM-B fusion and for measuring the resulting size, shape, polarity, etc. Methods are also known in the art to test whether the SOM-Bs are multipotential or plastic, that is, do they have the ability to differentiate into more than one cell type. Such studies can be performed using suspension, adherent, or spawned cells. Cellular phenotypes which can be studied include, but are not limited to, adipocytes, bone, cartilage, skeletal muscle, cardiac muscle, neural cells such as neurons, pancreatic islet cells, and endothelial cells.

Methods and reagents are also available for characterizing SOMBs, such as methods and reagents for performing immunocharacterization, including, but not limited to the markers and proteins: Oct 4, SSEA 3, SSEA 4, CD34, CD133, CD184, NG2, ABCG2, Nestin, MyoD, NKx2.5, Laminin, Beta1 integrin, Cbfa1, Collagen type II, MAPK, HLA-1 control, Insulin, Gata, Pax, Wnt, and other transcription factors and proteins. Flow cytometry markers include, CD34, NG2, ABCG2, CXCR4, CD271, CD140b, CD105, ALDH and HLA-1.

The present invention also provides methods for using SOMBs in vivo, and various techniques for using SOMBs in vivo are known to those of ordinary skill in the art. For example, SOMBs can be administered to a subject by various routes, including topically, subcutaneously, intramuscular, and direct administration. The SOMBs of the invention have a variety of uses, including, but not limited to, vascular remodeling, bone growth and regeneration, replacement use for tissues/cells such as pancreas/islets, central nervous system, skin repair and wound healing, peripheral nervous system, wounds, tendons, ligaments, muscle, organs such as liver and kidney, and lymph nodes, as well as in engraftment procedures.

SOM-Bs have novel implications and utility for various clinical and research areas, including, but not limited to:

1) basic science research, for the study of cell-cell interactions, cell-matrix interactions, morphogenesis/shape formation, apoptosis/anoikis, mesenchymal-epithelial, mesenchymal-stromal, and mesenchymal-endodermal interactions/crosstalk, malignant transformation, de-differentiation, transdifferentiation, asymmetric cell division;

2) diagnostics/assays, for use in stem cell assays, prediction of purity and potency of drugs, toxicology, efficacy of pharmaceuticals;

3) cell based therapeutics and regenerative strategies for damaged, injured, destroyed or aging tissues/organs, such as administration/use of SOM-Bs that are composed of a single cell type (such as ASCs), administration/use of SOM-Bs that are composed of multiple cell types/combinations, i.e., "hybrid SOM-Bs", for example, ASCs and Islet cells, or ASCs and osteoblasts, ASCs and HSCs, or ASCs with ectodermal cells such as keratinocytes, administration/use of combinations of SOM-Bs with dissociated cell suspension(s) of other cell types, such as a single cell type, or combinations of one or more cell types or dissociated cells derived from adherent cells and/or derived from SOM-Bs in suspension, as well as any and/or all of the above described cellular permutations used in combination with one or more of the following components, including, but not limited to, matrix factors, extracellular matrix molecules, growth factors, hormones, and bioactive factors; and 4) tissue engineering strategies for preparing, studying and using 2D or 3D constructs engineered from SOM-Bs and cell combinations outlined above (i.e., constructs of cell suspensions, SOM-Bs and/or scaffolds) 'pre-fabricated' prior to administration/implantation, as opposed to SOM-B/cell suspensions, which can be engineered based on polarity, position, phenotype, genetic alteration, etc., or seeded with/onto scaffolds of matrix/polymers etc. with or without bioactive factors. The terms hybrid SOM-Bs and chimeric-SOM-Bs are used interchangeably herein.

The SOM-Bs and the compositions and methods described herein also have use for regenerative therapies utilizing SOM-B-derived extracellular matrix, which has been processed and/or purified, with or without cells.

Conditioned medium derived from SOM-B cultures is useful of diagnostic purposes. It is also useful for regenerative therapies.

The data described herein suggests that ASC blastemas model ASCs in their native micro-niche more realistically than monolayer culture, and further suggests that they may better modulate tissue repair than single cell suspensions. Several real or potential advantages may be offered by administering ASCs prefabricated as 3-D niches (blastemas) as compared to more traditional single cell suspensions, including:

the cells have well-established cell-cell contacts and cell-matrix contacts, and are therefore less prone to anoikis. Anoikis is defined as programmed cell death induced by the loss of cell-matrix interactions, or by inappropriate cell-matrix interactions. (Valentijn et al., 2004; Michel, 2003). Anoikis may play a critical role in the low delivery and engraftment efficiency associated with various methods of cell delivery. Cell-to-cell interactions have been shown to be important for the differentiation of stem cells into various lineages, such as cardiomyocytes for example (Li et al., 2006);

the cells have generated their own extracellular matrix milieu and (presumably) associated growth factors (Wang et al., 2004);

"strength in numbers": the cells are able to survive and withstand severe in vitro conditions (such as serum-free culture) that are lethal to single cells in monolayer culture;

the cells are able to survive as a 3-D structure by diffusion (in culture) and presumably would be able to do the same after implantation to a wound/traumatic environment; and the cells retain the capacity to proliferate, migrate and/or morph in response to various external stimuli, suggesting they have the potential for dynamic interaction within an injured tissue milieu.

Antibodies may be generated using methods that are well known in the art. For instance, U.S. patent application Ser. No. 07/481,491, which is incorporated by reference herein in its entirety, discloses methods of raising antibodies to specific proteins. For the production of antibodies, various host animals, including but not limited to rabbits, mice, and rats, can be immunized by injection with a specific polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al, 1983, *Immunology Today* 4:72), and the EBV-hybridoma technique (Cole et al, 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals utilizing the technology described in international application no. PCT/US90/02545, which is incorporated by reference herein in its entirety.

In accordance with the invention, human antibodies may be used and obtained by utilizing human hybridomas (Cote et al., 1983, *Proc. Natl. Acad. Sci. U.S.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/ phage antibody libraries) are also included in the invention. Fab molecules comprise the entire 1 g light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxycarbonyl as the α-amino protecting group, and the FMOC method which utilizes 9-fluorenylmethyloxycarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Pharmaceutical compositions that are useful in the methods of the invention may be prepared, packaged, or sold in formulations suitable for administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient (i.e., cells, SOM-Bs, different sizes of SOM-Bs, etc.). The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. In addition to the active ingredient, a pharmaceutical composition of the invention may further comprise one or more additional pharmaceutically active agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, and intramuscular infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

The invention also includes a kit comprising the composition of the invention and an instructional material which describes administering or using the composition. In another embodiment, this kit comprises a (preferably sterile) solvent suitable for dissolving or suspending the composition of the invention prior to administering the composition.

As used herein, an "instructional material" includes a publication, a recording, a diagram, or any other medium of expression which can be used to communicate the usefulness of the invention in the kit for effecting enrichment and growth of adipose stem cells. Optionally, or alternately, the instructional material may describe one or more methods of alleviation the diseases or disorders in a cell or a tissue of a mammal. The instructional material of the kit of the invention may, for example, be affixed to a container which contains the compositions of the invention or be shipped together with a container which contains the antibody. Alternatively, the instructional material may be shipped separately from the container with the intention that the instructional material and the compound be used cooperatively by the recipient.

EXAMPLES

General Methods

The adipose tissue-derived stem/stromal cells useful in the methods of invention can be isolated by a variety of methods known to those of ordinary skill in the art. A preferred source of adipose tissue is subcutaneous adipose. In humans, the adipose is typically isolated by liposuction.

Human adipose tissue-derived adult stem/stromal cells represent a cell source that can be harvested routinely with minimal risk or discomfort to the patient. They can be expanded ex vivo, differentiated along unique lineage pathways, genetically engineered, and re-introduced into individuals as either autologous or allogeneic transplantation.

Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells are obtained from minced human adipose tissue by collagenase digestion and differential centrifugation (Halvorsen et al 2001, Metabolism 50:407-413; Hauner et al 1989, J Clin Invest 84:1663-1670; Rodbell et al 1966, J. Biol. Chem. 241:130-139). Others have demonstrated that human adipose tissue-derived stromal cells can differentiate along the adipocyte, chondrocyte, and osteoblast lineage pathways (Erickson et al 2002, Biochem. Biophys. Res. Commun. Jan. 18, 2002; 290(2):763-9; Gronthos et al 2001, Journal of Cellular Physiology, 189:54-63; Halvorsen et al 2001; Metabolism 50:407-413; Halvorsen et al, 2001, Tissue Eng. Dec. 7, 2001; (6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517; Zuk et al 2001, Tissue Eng. 7:211-223). Other useful techniques are also available.

The above-identified methods can be used to isolate adipose tissue and adipose stem cells.

The experiments described below were begun based on the observation by the inventors that ASCs sometimes form discrete cellular "clusters" or "nodules" of cells in monolayer culture conditions.

Media Development

DMEM/F12 was chosen for use in the original base medium as described in PCT Application PCT/US06/34915 (Katz and Parker; filed Sep. 8, 2006) which claims the benefit of priority of U.S. Provisional Application Nos. 60/715,025 and 60/716,337 filed Sep. 8, 2005 and Sep. 12, 2005, respectively, the disclosures of which are incorporated herein in their entirety. A continually enriched medium was developed through stepwise addition of individual ingredients, demonstrated to increase the proliferation rates of ASCs. Table 1 summarizes this process and the list of ingredients screened at each iteration.

TABLE 1

Media Formulations

| Formulation | Modifications Screened | Resulting Base |
| --- | --- | --- |
| AR | N/A | DMEM/F12, L-glutamine, dexamethasone, ascorbic acid 2-phosphate, ITS + 3, fatty acid supplement, non-essential amino acids, antibiotic-antimycotic |
| AR2 | AR + (EGF, PDGF, bFGF or gluten peptone) | AR + PDGF + EGF |
| AR3 | AR2 + (bFGF, FLT-3 ligand, HGF, IGF-1, SCGF-β, SDF-1, VEGF, SCF, hydrocortisone, estradiol, progesterone, TNFα, IL-1β or human serum) | AR2 + 0.5% human serum |

TABLE 1-continued

Media Formulations

| Formulation | Modifications Screened | Resulting Base |
|---|---|---|
| AR4 | AR3 + (bFGF, FLT-3 ligand, HGF, IGF-1, SCGF-β, SDF-1, VEGF, SCF, hydrocortisone, estradiol, progesterone, TNFα or IL-1β) | AR3 + SCGF-β + TNFα |
| AR5 | AR4 + (bFGF, FLT-3 ligand, HGF, IGF-1, SDF-1, VEGF, SCF, hydrocortisone, estradiol, progesterone, IL-1β or TGF-β1) | AR4 + estradiol + progesterone |
| AR6 | AR5 + (bFGF, FLT-3 ligand, HGF, IGF-1, SDF-1, VEGF, SCF, hydrocortisone, IL-1β or TGF-β1) | AR5 + IL-1β + hydrocortisone |
| AR7 | AR6 + (peptones PPA, PPB, WPA, SPA, SPB, YE, UFYE, MER2, MER3, CPN1 or GPN3); substituting ITS for ITS + 3, & AR6 at modified concentrations | AR6 at modified concentrations |
| AR8 | AR7 at modified concentrations | see table 2 |

The final recipe, which was tested in the subsequent work, includes the base medium DMEM/F12 supplemented with five growth factors, four hormones, several nutritional supplements, and the optional supplementation with 0.5% human serum (Table 2). Table 2 summarizes studies which started with an initial base recipe, and then modifications were screened individually for their ability to enhance cell proliferation. Those modifications demonstrating a statistically significant increase in proliferation compared with the starting formula were added to a new base recipe. This was repeated in a stepwise fashion leading to the development of a rich basal media.

The base medium ingredients of the invention are provided in Table 2, which comprises DMEM/F12 and the ingredients listed in Table 2.

TABLE 2

General Medium Formulations of the Invention

AR8 Base Recipe
DMEM/F12 (with glutamine)

| | |
|---|---|
| 0.1 mM | L-glutamine |
| $1 \times 10^{-8}$ M | Dexamethasone |
| 100 μM | Ascorbic acid 2-phosphate (ASAP) |
| 0.50% | ITS + 3 |
| 0.05% | Fatty acid supplement |
| 1% | NEAA (non essential amino acids) |
| $1 \times 10^{-8}$ M | Estradiol |
| $1 \times 10^{-8}$ M | Progesterone |
| 500 ng/ml | Hydrocortisone |
| 10 ng/ml | EGF |
| 1 ng/ml | PDGF |
| 1 ng/ml | SCGF-β |
| 1 ng/ml | TNF-α |
| 1 ng/ml | IL-1β |
| 1% | Antibiotic antimycotic |
| 0.5% | Human serum (optional) |

AR9 substitute ITS + 3 of AR8 for:

| | |
|---|---|
| 1.0 mg/ml | insulin |
| 0.55 mg/ml | human transferrin |
| 0.5 μg/ml | sodium selenite |
| 470 μg/ml | linoleic acid |
| 470 μg/ml | oleic acid |
| 50 mg/ml | human serum albumin |

Briefly, the basic components include: DMEM/F12, antibiotics, nutrients (amino acids, fatty acids, minerals), growth factors, and/or hormones, and or adhesion factors. Several types of albumin were tested.

Preparation of the medium of Table 2 includes the use of: 500 ml of DMEM/F12 (Gibco Cat No. 11320-033; Invitrogen Corp), 250 μl L-glutamine (Gibco Cat No. 25030-081, Invitrogen Corp), 5 ml Antibiotic Antimycotic (Gibco Cat No. 15240-062, Invitrogen Corp), 2.5 ml ITS+3 (Sigma 1-2771), 250 μl fatty acid supplement (Sigma F-7050), 5 ml MEM non-essential amino acids (Gibco Cat No. 11140-050, Invitrogen Corp), 50 μM ASAP (Sigma A-8960), 1 ng/ml PDGF-BB (Research Diagnostics Inc., RDI-114b), 10 ng/ml EGF (R & D Systems 236EG), 1 ng/ml SCGF-β (Research Diagnostics Inc. RDI-1022B), 1 ng/ml TNFα (Research Diagnostics Inc., RDI-301), 1 ng/ml IL-1β (Research Diagnostics Inc., RDI-201B), $1 \times 10^{-8}$ M β-estradiol (Sigma E2758-1G), $1 \times 10^{-8}$ M progesterone (Sigma P8783-5G), $1 \times 10^{-8}$ M dexamethasone (Sigma D-8893), and 500 ng/ml hydrocortisone (Sigma H0888-1G). AR9 medium preparation substitutes the ITS+3 of AR8 with the ingredients of the right column of Table 2.

Preparation and Characterization of Mesenchymal Stem Cells Aggregates

Methods

Formation of Self Organizing Mesenchymal Blastemas (SOM-Bs):

Low passage ASCs in monolayer cultures were pre-labeled with DiI or DiO (Molecular Probes) per manufacturer's instructions (cells were rinsed to remove serum, if present, and incubated in 1:200 representative dye solution in serum-free media for 15 minutes at 37° C., and subsequently rinsed again to remove excess dye).

Cells were treated with trypsin to detach from plastic. A pellet was obtained following centrifugation. The cells were diluted in the appropriate volume of medium (DMEM/F12+ 10% FBS or chemically defined low-serum or serum free) for desired dilutions. Varied volumes (15-30 μl) of media containing the desired number of cells (500-50,000) were pipetted onto culture plate covers. In some experiments, the culture plate covers were flipped upside down to result in "hanging droplets".

Plates were placed in humid chambers to prevent media from drying out. The droplets were maintained in standard tissue culture incubators for 48 hours.

Resulting spheres/SOM-Bs were transferred by pipette into Ultra Low Attachment (ULA) wells/plates (Corning). Some SOM-Bs were plated in 96 well plates at one SOM-B per well to record the changes in individual SOM-Bs over time. Some SOM-Bs were plated in 12 and 24 well ULA plates as groups of multiple SOM-Bs per well.

A variation of the method is to form the drops containing ASCs on the bottoms of ULA plates. Following SOM-B formation in droplets the plates may be turned right side up and filled with the goal media to place the SOM-Bs in suspension. This procedure avoids manual handling of SOM-Bs.

Figure 9:
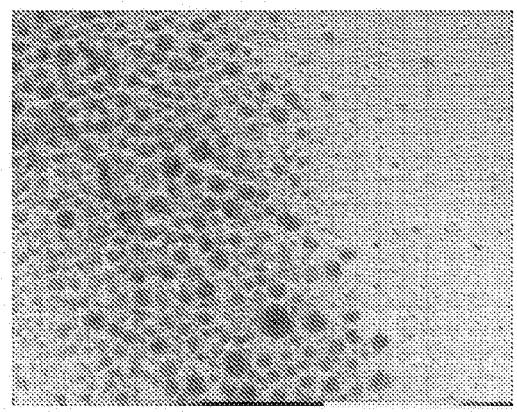
FIG. 9, comprising left and right panels, represents images of photomicrographs demonstrating an alternative to the "Droplet Method": ASCs were induced to form SOM-Bs when plated at very high density in Ultra Low Attachment Plates.
Figure 9:
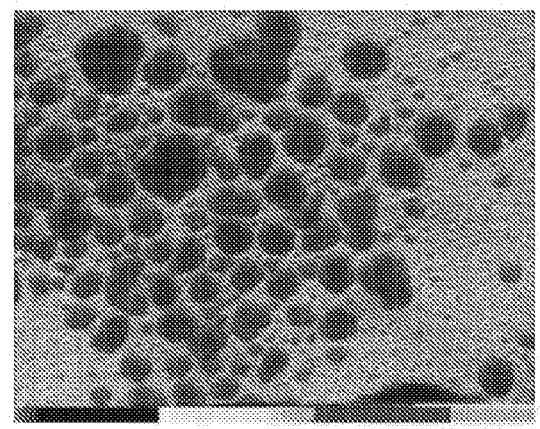

Another variation of the method is to form SOM-Bs by suspension or pre-determined numbers of ASCs in media at high density in ULA plates, and subsequent sorting of resultant SOM-Bs based on their size (see FIG. 9).

Following formation, SOM-Bs were plated in wells containing different media: DMEM/F12 with no serum; DMEM/F12+10% FBS, AR media version 6 (AR6) with no serum; AR6 with 1% human serum; AR media version 8 (AR8) with no serum; AR8+0.5% human serum; and AR8+1% human serum. All media contained 1% antibiotic. Media were replaced regularly. SOM-Bs were photographed at regular intervals to track changes in size and polarization. The results demonstrate that SOM-Bs can be maintained in respective media for up to 3 months or longer.

In some experiments, SOM-Bs were labeled with Hoechst 33342 dye to reveal distribution of cells as follows: SOM-Bs were rinsed with PBS and incubated in 4 µM dye solution for 15 min in the dark at 37° C. SOM-Bs were subsequently rinsed with PBS and placed in appropriate media (see FIG. 14C). Bromodeoxyuridine (BrdU) was used to label cells in some experiments as an indicator of cell proliferation.

For cryosectioning, SOM-Bs were fixed for 3-12 hours in 10% formalin, followed by a 3-12 incubation in 30% sucrose in PBS, and then flash frozen in cold isopentane. SOM-Bs were sectioned at 10 µm and processed for H and E staining (FIG. 13), Oil Red O staining, Alizarin Red staining, and/or immunohistochemistry. To test for spontaneous SOM-B formation, ASCs were left in suspension in DMEM/F12 containing 10% FBS or in serum-free AR8 in ULA culture plates at a very high cell density that allowed for a "super-confluent" layer of floating cells. Plates were examined periodically using microscopy to monitor and record spontaneous formation of SOM-Bs (FIG. 9).

Results

I. ASCs can be Reliably and Reproducibly Formed into 3-Dimensional Multicellular Aggregates in a Controlled Manner Using Several Different Approaches.

The studies disclosed below demonstrate the successful formation of ASC spheroids (blastemas) using varied numbers of early passage ASCs (from 500 to 50,000) isolated and cultured from multiple donors using a hanging drop method. The blastemas formed in a range of media volumes (15-30 microliters) as well as in a variety of media types, including DMEM/F12 with 10% FBS, DMEM/F12 with no other additives, serum-free ASC medium (AR8), or low serum ASC medium (AR8 with 0.5-1% serum, either human or fetal bovine). Multiple small clusters/spheroids formed in the hanging drops when 500 or 1000 ASCs were used for spheroid formation. In contrast, large, single blastemas of consistent size formed at 95% or higher efficiency when high numbers of cells were used (2,000, 5,000 and higher). FIG. 1 demonstrates the initial clustering and appearance of a typical SOM-B soon after formation using a hanging drop technique. Using the hanging drop method, ASCs typically organized into discrete spheroids within 24-72 hours (FIG. 2), and could be reliably transferred to suspension or adherent culture conditions thereafter without damage to or loss of form. FIG. 2 demonstrates a photomicrograph of multiple well-defined, uniform sized SOM-Bs composed of fluorescently labeled (DiI) ASCs soon after their transfer to suspension culture. In contrast, FIGS. 9 and 15 depict the variable range in blastema sizes that can be fabricated depending on cell numbers used and time spent in a hanging drop. Of note, panel D shows the appearance of 'mini-SOM-Bs' within the barrel of a 20 microliter Hamilton microsyringe, thereby demonstrating the ability to control/manipulate the size of the SOM-Bs for in vivo delivery objectives. When fewer than 5,000 cells are used in the hanging drop technique, multiple 'mini-SOM-Bs' of varied sizes form rather than one large, well-defined sphere; about 5,000 cells or higher seems to be required for the formation of SOM-Bs of predictable and reproducible size.

ASC blastemas can also be formed by culturing ASCs at very high densities in suspension using ultra low attachment plates. Using this method, the floating layer of ASCs self-aggregate over a period of 24-72 hours, in a variety of culture media similar to those mentioned above. Unlike the hanging drop technique, blastemas that form using this method are not as uniform in size, and the number of ASC per aggregate is not defined. FIG. 9 shows two panels that demonstrate the formation of ASC blastemas using the 'high density floating cell' technique described.

Additional studies were performed to evaluate the effect of cell culture/cell passage and the impact of enriched ASC subpopulations on blastema formation. It was found that SOM-Bs were able to form with ASCs that were freshly isolated and had never touched plastic. These SOM-Bs displayed formation, adherence, and "spawning" properties that were similar to spheres formed from cells grown in adherent monolayer culture for one or two passages.

Additional studies were performed to test for SOM-B formation from $5 \times 10^2$, $1 \times 10^3$, $2 \times 10^3$ and $5 \times 10^3$ FACS-sorted ASCs. The cells were sorted into subpopulations according to presence or absence of extracellular antigen CD34 and intracellular ALDH as follows: ALDH$^+$ only, ALDH$^-$ only, CD34$^+$/ALDH$^+$, CD34$^+$/ALDH$^-$, CD34$^-$/ALDH$^+$, CD34$^-$/ALDH$^-$. There were no observed differences in the frequency of SOM-B formation between all these groups, suggesting that the presence or absence of CD34 and ALDH did not pre-select for cells that were more or less capable of aggregation and SOM-B formation (Table 3).

TABLE 3

SOM-B formation from sorted ASCs.

| Cell number | Sorting Marker | | | | | |
|---|---|---|---|---|---|---|
| | ALDH$^+$ | ALDH$^-$ | CD34$^+$ ALDH$^+$ | CD34$^+$ ALDH$^-$ | CD34$^-$ ALDH$^+$ | CD34$^-$ ALDH$^-$ |
| $5 \times 10^2$ | − | + | + | + | + | + |
| $1 \times 10^3$ | − | + | + | + | + | + |
| $2 \times 10^3$ | − | + | + | + | − | + |
| $5 \times 10^3$ | + | − | − | − | + | − |

II. ASC Blastemas are Composed of Cells and Variable Amounts of Self-Generated Extracellular Matrix.

Figure 13A:
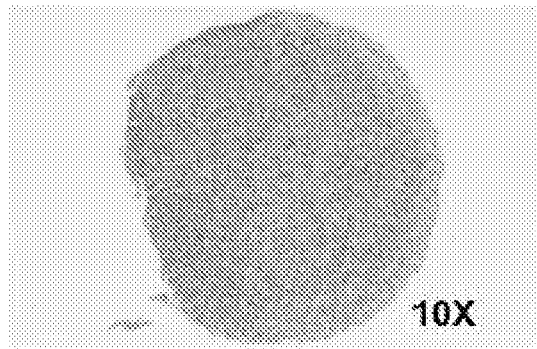
FIG. 13, comprising FIGS. 13A and 13B, FIG. 13B further comprising left and right panels, represents images of photomicrographs. H&E staining of SOM-B 14 days following formation reveals a uniform distribution of apparently viable cells that are embedded in self-generated extracellular matrix throughout the sphere, with possible specialization of cells at the sphere's border.
Figure 13B:
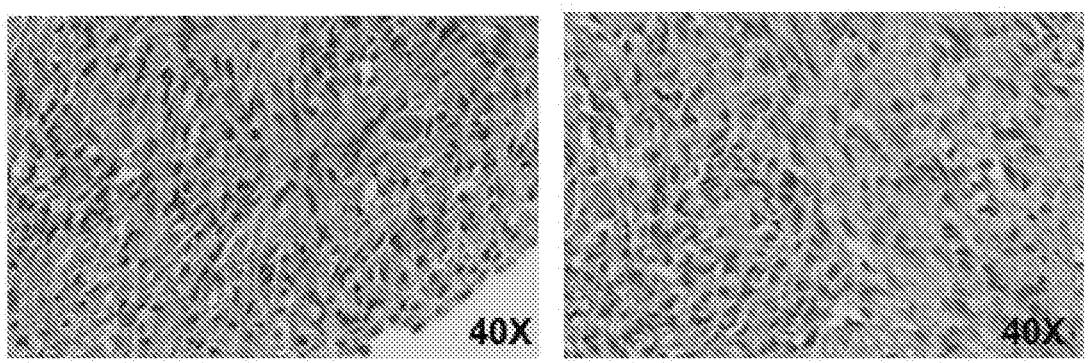
Figure 14A:
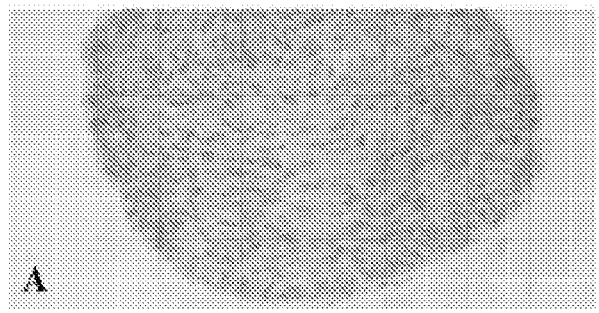
FIGS. 14A-C, represents images of photomicrographs. H&E staining (A) reveals that there does not appear to be a cell density difference between the original DiI-positive "core" (B) from which the cells proliferated and the rest of SOM-B. Hoechst staining of "live" SOM-Bs (C) also reveals a fairly uniform distribution of cells throughout the sphere.
Figure 14B:
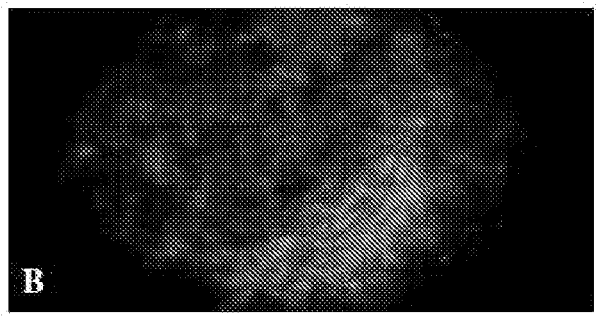
Figure 14C:
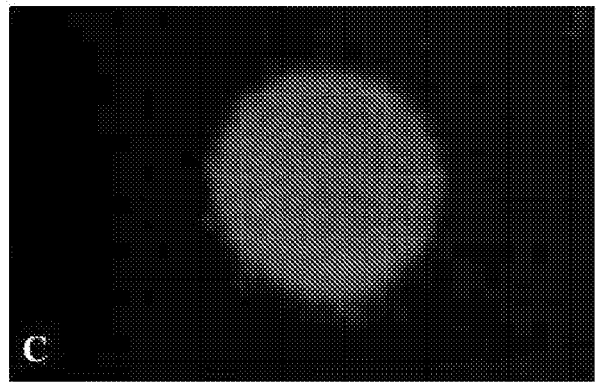
Figure 15A:
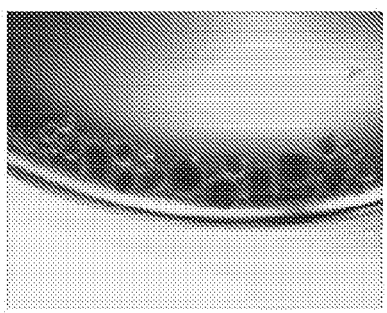
FIG. 15, comprising four panels (A-D), represents images of photomicrographs demonstrating that SOM-B size may be adjusted for specific applications, such as for delivery in vivo to wounds, etc. The resulting SOMBs may provide the optimal configuration for cell therapy, while being small enough to fit into a 10 μl Hamilton microsyringe barrel (15D).
Figure 15B:
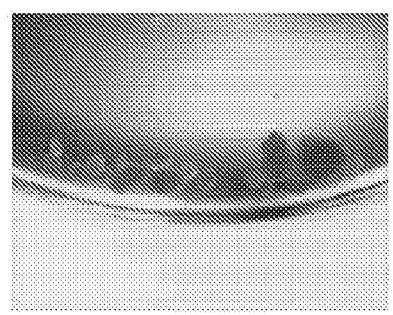
Figure 15C:
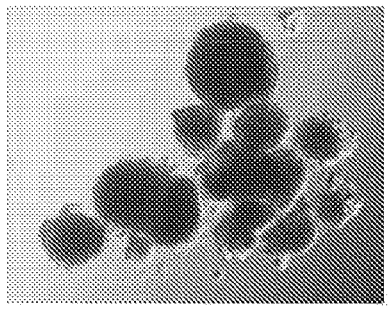
Figure 15D:
Figure 16:
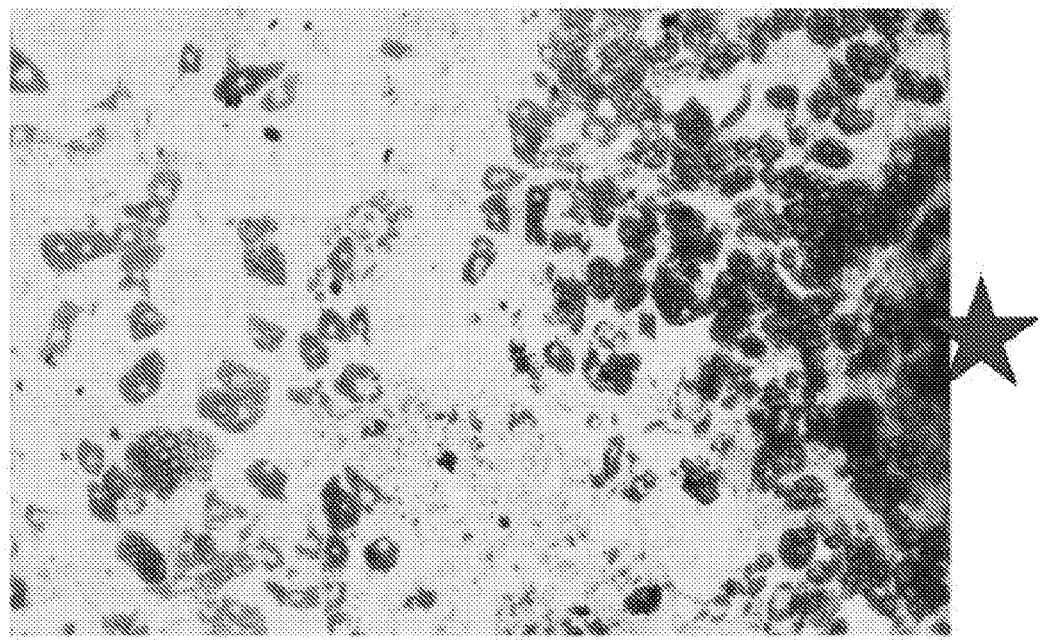
FIG. 16 represents an image of a photomicrograph demonstrating Oil Red O staining of SOM-B-derived mouse ASCs cultured in adipogenic media for 14 days (star indicates location of SOM-B attachment to culture plate).
Figure 17:
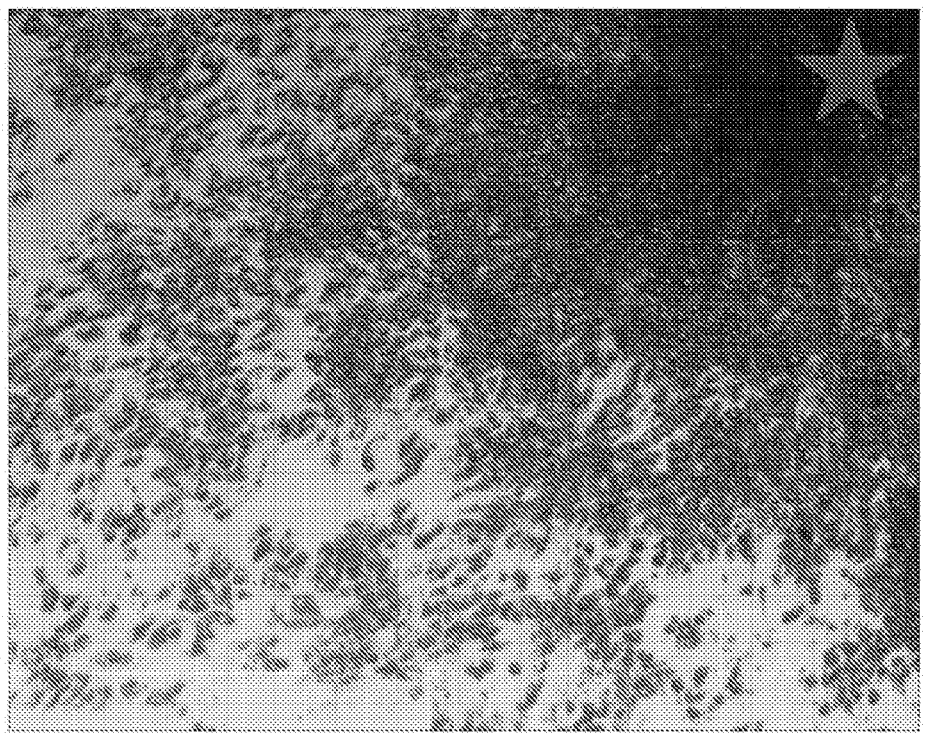
FIG. 17 represents an image of a photomicrograph demonstrating Oil Red O staining of SOM-B-derived human ASCs cultured in adipogenic media (star indicates location of SOM-B attachment to culture plate), following second consecutive SOM-B "transplant" and re-attachment.
Figure 18:
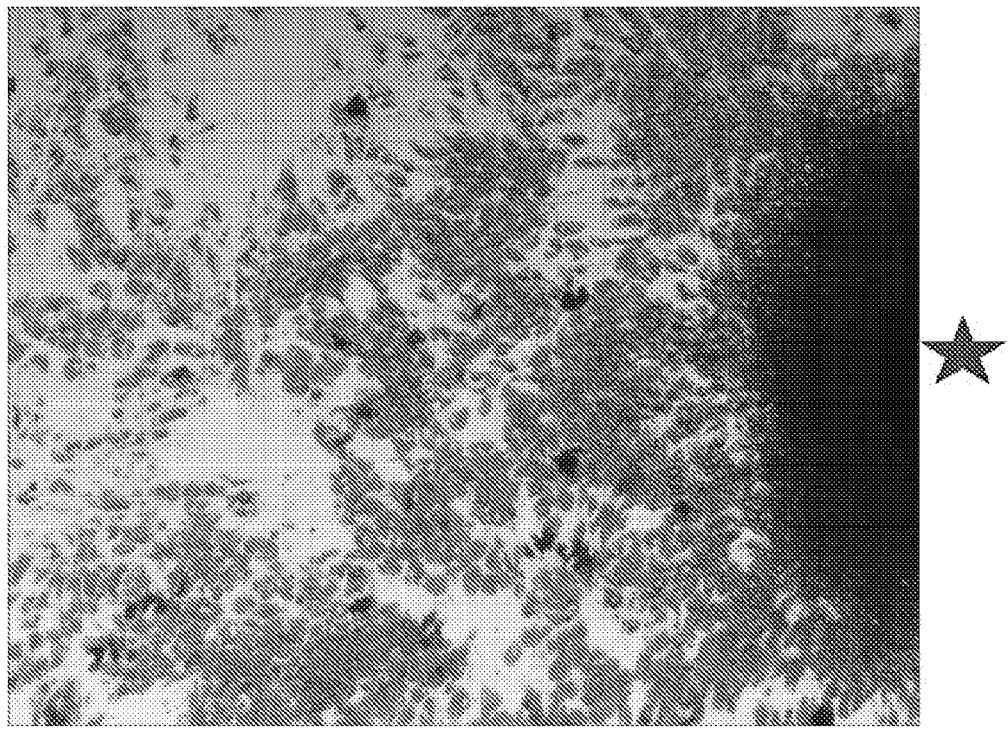
FIG. 18 represents an image of a photomicrograph demonstrating Oil Red O staining of SOM-B-derived human ASCs cultured in adipogenic media (star indicates location of SOM-B attachment to culture plate), following third consecutive SOM-B "transplant" and re-attachment.
Figure 20A:
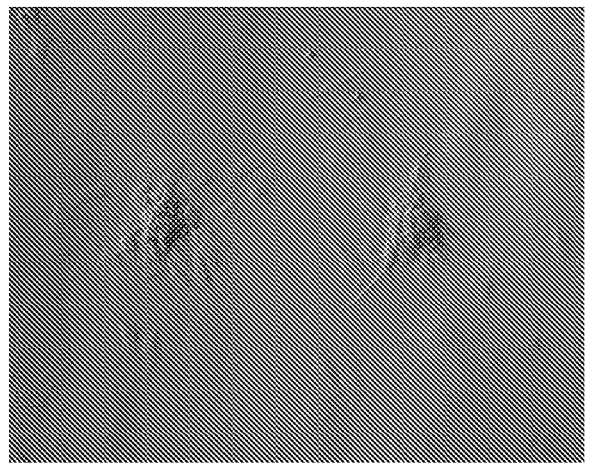
FIGS. 20A to 20C, represents phase contrast images demonstrating small clusters of attached ASCs, which in time give rise to a large progeny of cells (20A to 20C).
Figure 20B:
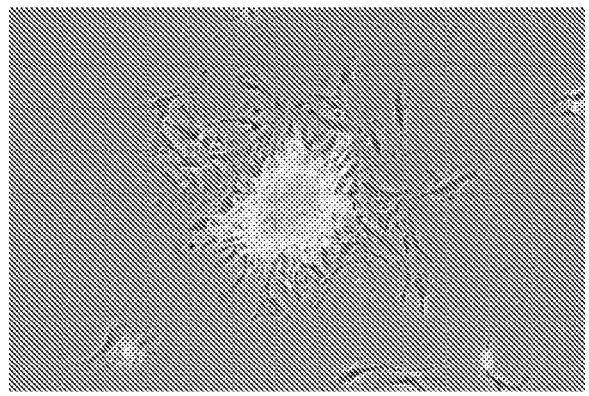
Figure 20C:
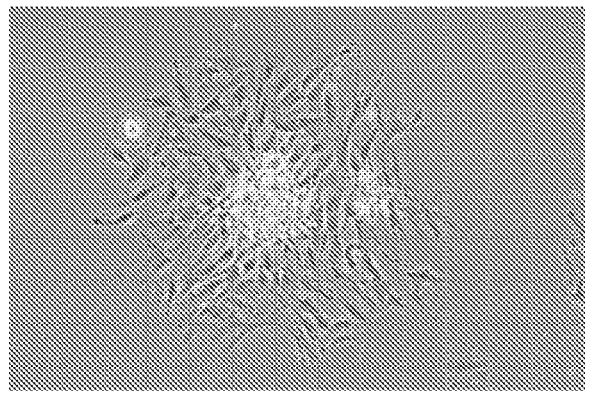
Figure 21:
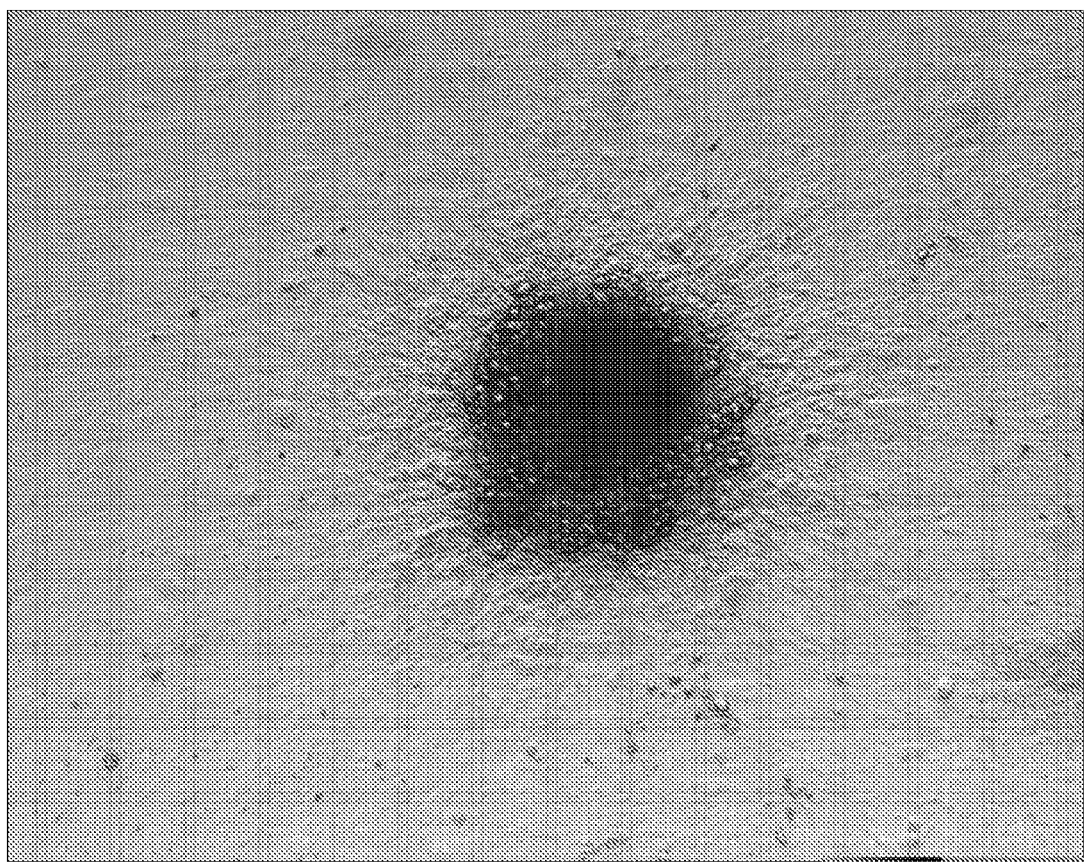
FIG. 21 represents a photomicrographic image of attached ASC SOM-Bs, demonstrating that when first grown in low serum (1% human serum) medium, then in 10% FBS medium, there is robust differentiation of cells within SOM-Bs into adipocytes in the absence of adipogenic media.

To determine the cellularity and cellular topography of SOM-B's, Hoechst stain was used to label nuclei. This revealed extensive and apparently non-compromised cellularity throughout the SOM-B (see FIG. 14C). To further evaluate the cellularity and architecture of SOM-Bs, some SOM-Bs were fixed, sectioned, and stained. This work revealed structures with fairly uniform cellularity and abundant extracellular matrix. As seen in FIGS. 13, 14 and 19, H and E staining of representative SOM-Bs maintained in either DMEM/F12-0% serum, DMEM/F12-10% FBS, or AR+0% serum suggest that the SOM-Bs increase in size is a result of robust cell proliferation and/or extracellular matrix production. In addition, the outermost layer of cells of the SOMB seems to have an epithelial, or columnar appearance, raising the question of epithelial transformation of these cells. Differential cell growth within the SOM-B is reflected in the differential (i.e., polarized) fluorescence visualized in FIG. 14B.

Several studies were performed to determine how to best dissociate formed SOM-Bs. SOM-Bs were subjected to a variety of compounds and procedures in efforts to isolate their cellular components. These included trypsin, collagenase, and mechanical dissociation/agitation of SOM-Bs. The SOM-Bs were found to be exceptionally robust and durable, resisting mechanical dissociation strategies. Enzymatic compounds (collagenase, trypsin, etc.) produced the best dissociation, further reflecting the presence of an established extracellular matrix milieu within the SOM-B.

III. ASC Blastemas can be Maintained for Prolonged Periods in Adherent Culture and Demonstrate a Capacity for Extensive Self-Renewal in Adherent Culture Conditions.

Figure 10A:
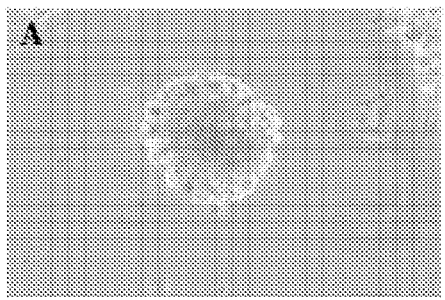
FIGS. 10A-10D, represents images of photomicrographs demonstrating that SOM-Bs (10A and 10B) attach to tissue culture plastic by "anchoring" with cell processes that extend from SOM-Bs. Following attachment SOM-Bs "spawn" cells which eventually repopulate the culture place (C). SOM-Bs may be lifted off the plate (star in D) and re-plated repeatedly for generation of new cells.
Figure 10B:
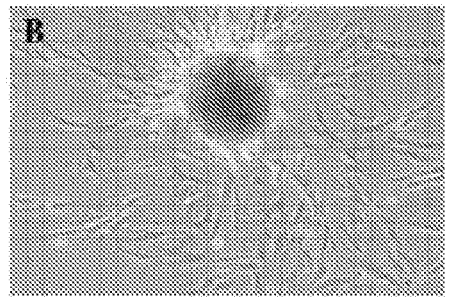
Figure 10C:
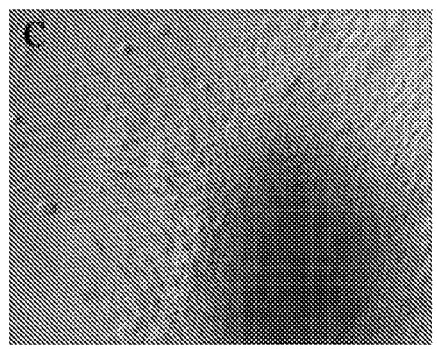
Figure 10D:
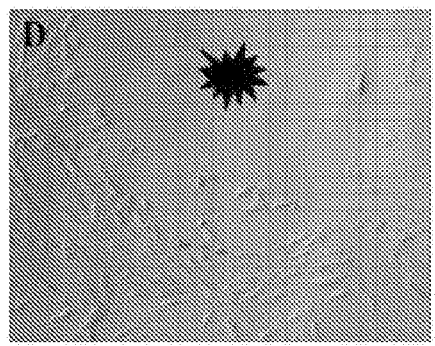
Figure 11:
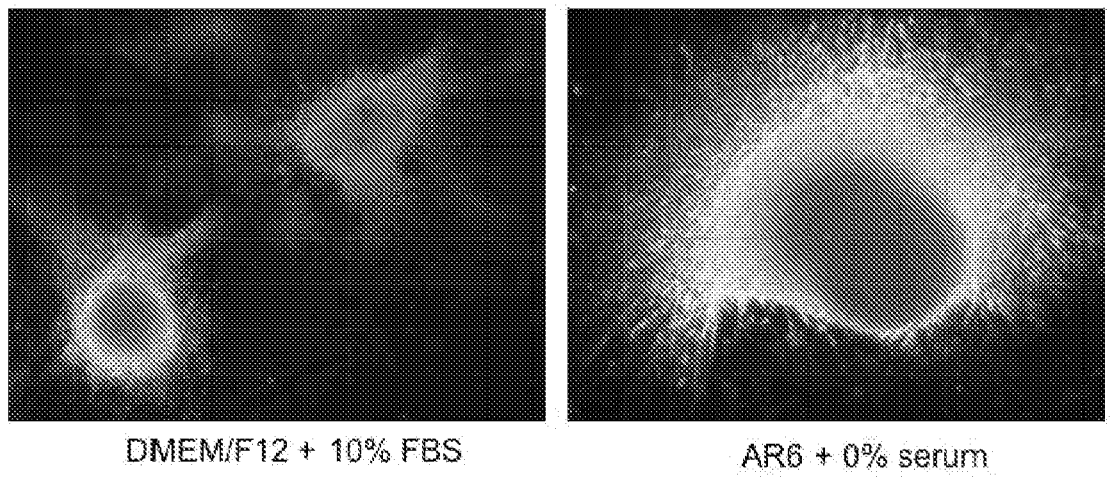
FIG. 11, comprising left and right panels, represents images of photomicrographs demonstrating attachment, anchoring, and spawning of cells by SOM-Bs grown in DMEM/F12+10% or AR-type media+0% serum.

When plated onto regular tissue culture plates, SOM-Bs became "anchored" to the plastic by cell processes, which extend out of SOM-Bs (See FIG. 8). SOM-Bs may migrate in a complex pattern on the plates' surface, apparently by differential adhesion and release of anchoring cell processes. Shortly after adhesion, SOM-Bs "spawn" progeny cells around the perimeter (see FIGS. 10B, 11A, and 11B). Cells continued to proliferate out of SOM-Bs and populate the host plate to confluence (see FIG. 10C). Furthermore, adherent SOM-Bs could be lifted from culture and transferred, or passaged to a new culture vessel where it was found that they would readily attach and spawn additional progeny. The inventors have passaged such adherent SOM-Bs nearly 30 times at the time of this writing, and although the generation of progeny cells has diminished with passages 20 or higher, they continue to generate monolayer ASCs that grow to confluence and that maintain multilineage developmental plasticity (tested up through~passage 15 cells to date).

IV. ASC Blastemas can be Maintained for Prolonged Periods in Suspension Culture and Display Robust Survival Capacity when Grown in Various Serum-Free Suspension Culture Conditions.

Figure 22:
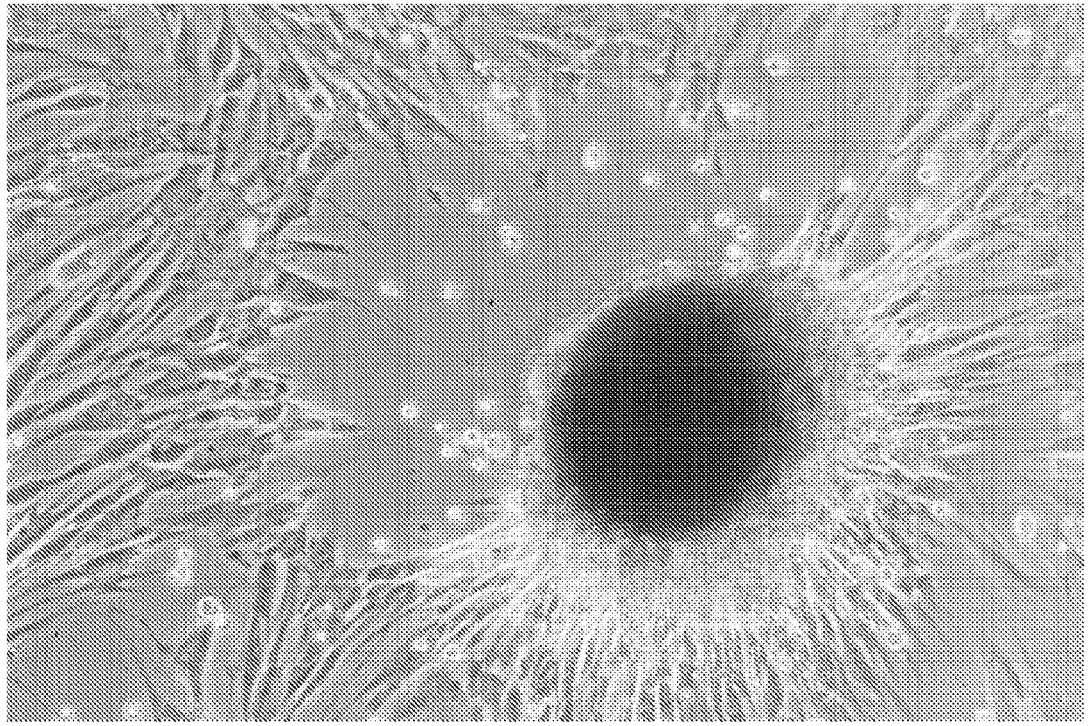
FIG. 22 represents a photomicrographic image demonstrating that attached ASCs may be induced to form SOM-Bs when placed in serum-free media. Cells which do not coalesce into SOM-Bs will eventually detach and die.
Figure 23A:
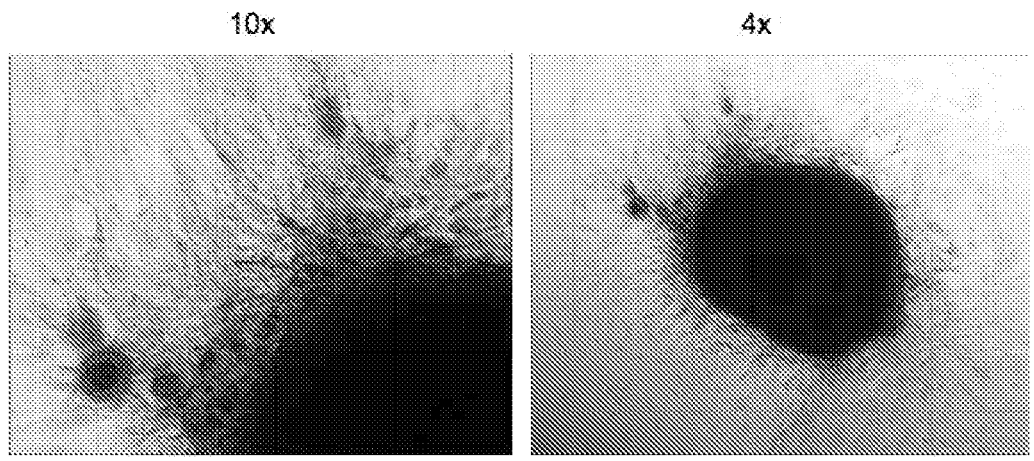
FIG. 23, comprising four panels (FIG. 23A-*upper* left, 10× magnification; upper right, 4× magnification.
FIG. 23B-*lower* left, 10×; lower right, 4×), represents photomicrographic images of ASC blastemas grown in serum-free AR8 medium in suspension culture for 4 weeks. They were then transferred to adherent culture. After 4 days in adherent culture, the blastemas were exposed to either adipogenic medium or osteogenic medium for another 14 days. The cultures were then fixed and stained. The top panel images show extensive alizarin red staining in blastemas grown in osteogenic medium. The bottom panel images show free lipid droplets and positive Oil Red O staining in blastemas grown in adipogenic medium.
Figure 23B:
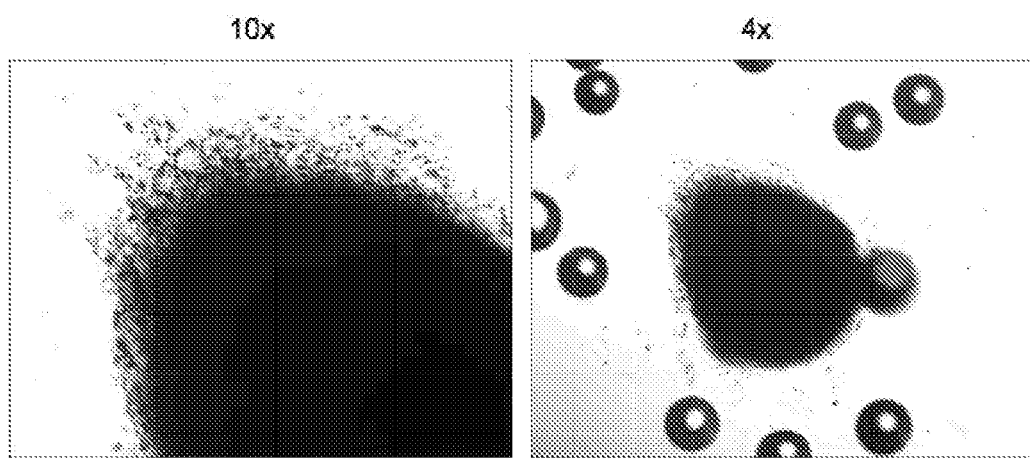
Figure 24A:
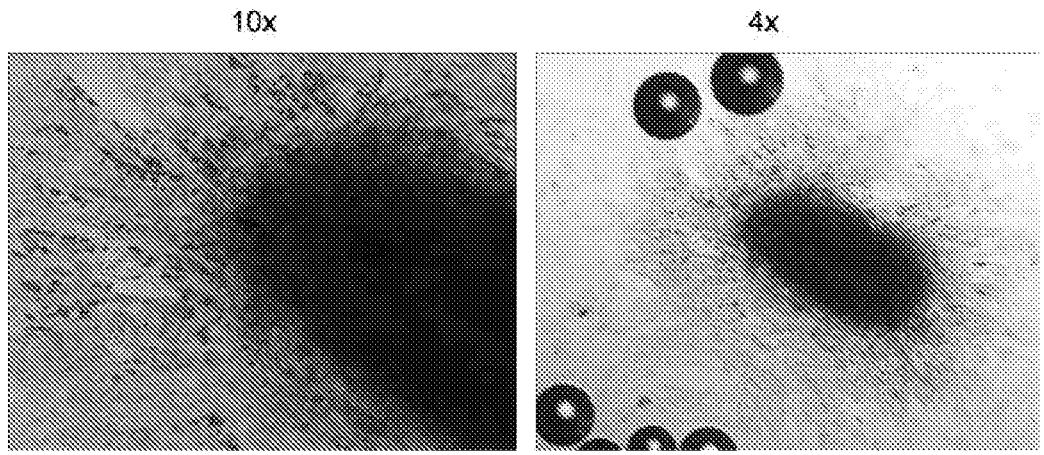
FIG. 24, comprising four panels (FIG. 24A-*upper* left, 10×; upper right, 4×.
FIG. 24B-*lower* left, 10×; lower right, 4×), represents photomicrographic images of ASC blastemas grown in DMEM/F12+10% FBS medium in suspension culture for 4 weeks. They were then transferred to adherent culture. After 4 days in adherent culture, the blastemas were exposed to either adipogenic medium or osteogenic medium for another 14 days. The cultures were then fixed and stained. The top panel images show extensive alizarin red staining in blastemas grown in osteogenic medium. The bottom panel images show free lipid droplets and positive Oil Red O staining in blastemas grown in adipogenic medium.
Figure 24B:
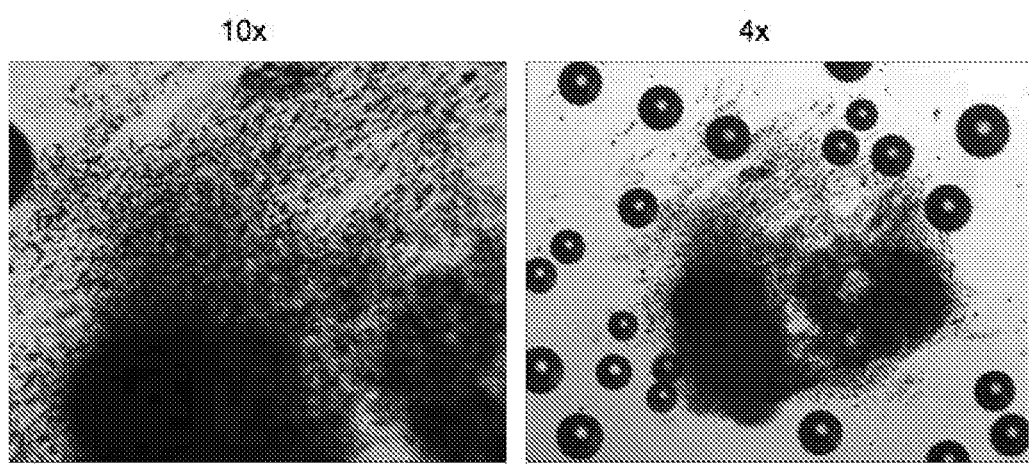
Figure 25A:
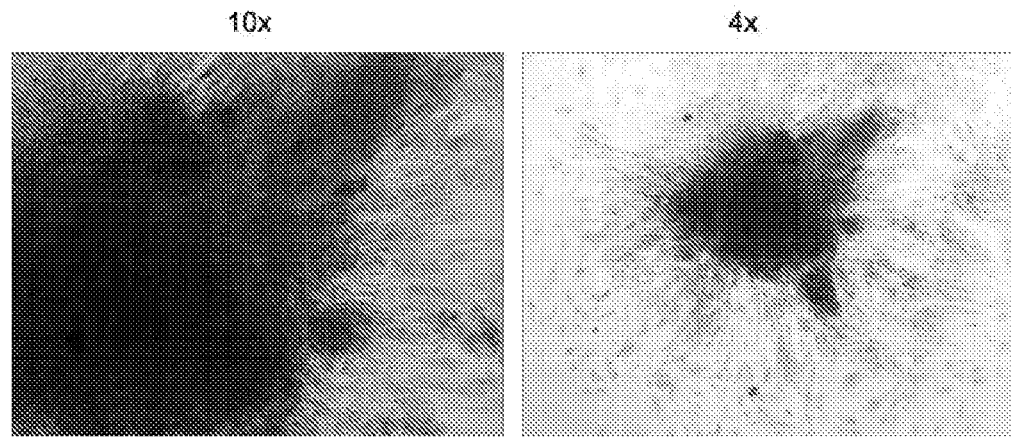
FIG. 25, comprising four panels (FIG. 25A-*upper* left, 10×; upper right, 4×; lower left, 10×.
FIG. 25B-*lower* right, 4×), represents photomicrographic images of ASC blastemas grown in unsupplemented DMEM/F12 medium with no serum-free in suspension culture for 4 weeks. They were then transferred to adherent culture. After 4 days in adherent culture, the blastemas were then cultured for 14 days in either adipogenic medium or osteogenic medium. The cultures were then fixed and stained. The top panel images show extensive alizarin red staining in blastemas grown in osteogenic medium. The bottom panel images show free lipid droplets and positive Oil Red O staining in blastemas grown in adipogenic medium.
Figure 25B:
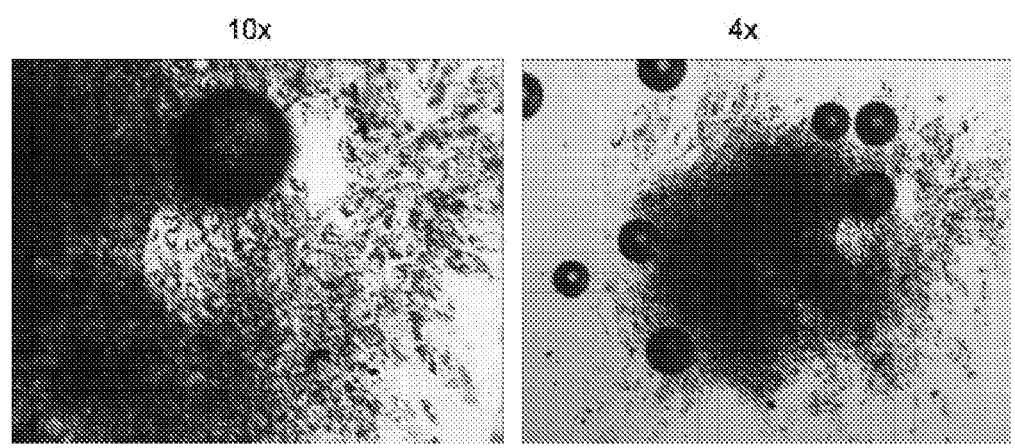
Figure 26A:
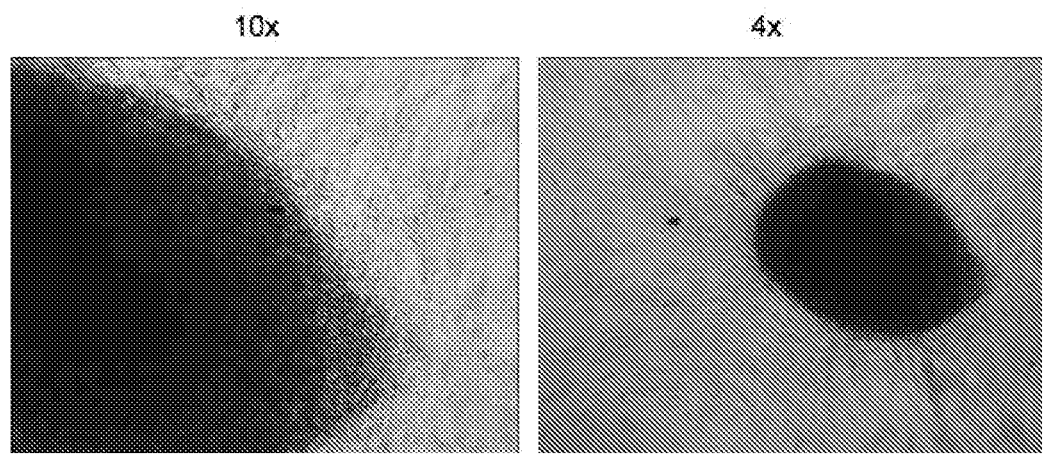
FIG. 26, comprising four panels (FIG. 26A-*upper* left, 10×; upper right, 4×.
FIG. 26B-*lower* left, 10×; lower right, 4×), represents photomicrographic images of ASC blastemas grown in DMEM/F12+10% FBS medium in suspension culture for 4 weeks. They were then transferred to adherent culture. After 4 days in adherent culture, the blastemas were cultured for another 14 days in DMEM/F12+10% FBS medium to serve as a control group. The cultures were then fixed and stained. The top panel images show alizarin red staining in blastemas grown in control medium. The bottom panel images show Oil Red O staining in blastemas grown in control medium.
Figure 26B:
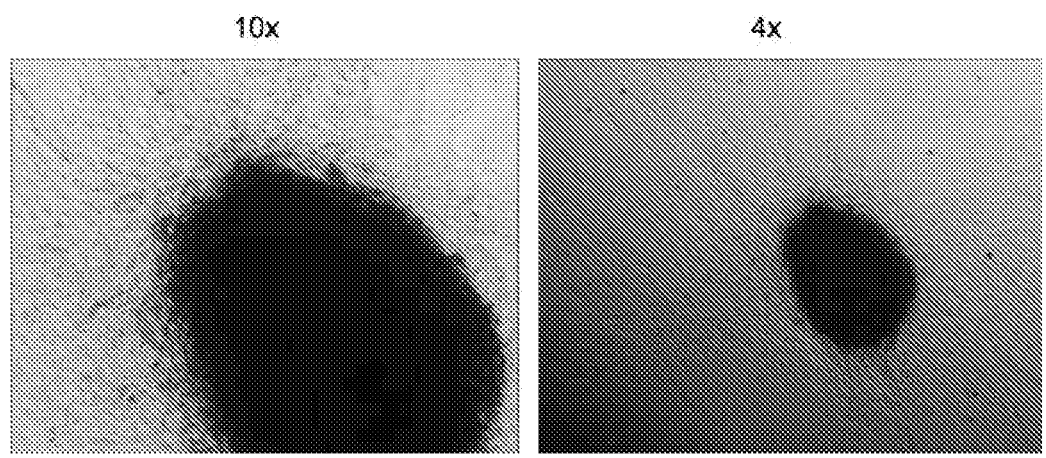

ASC blastemas can also be cultured successfully in suspension (i.e., floating) culture using ULA cultureware. SOM-Bs can survive for at least 3 months (the longest tested) in suspension culture, based on microscopic appearance, H and E histology, and their ability to spawn new cells when placed into adherent culture. Even SOM-Bs grown in DMEM-0% serum for as long as one month maintained their compact architecture under microscopic evaluation, as well as DiI fluorescence. In addition, when such SOM-Bs were plated onto regular tissue culture plates, they readily attached to plastic and spawned cells, indicating that even when SOM-Bs are maintained in unsupplemented DMEM/F12 media without serum or other additives, cells are able to survive. Again, this suggests a niche environment capable of sustenance and renewal, even in the most minimalistic of culture conditions. Interestingly, SOM-Bs were also observed to form spontaneously in low-serum or serum-free media (see FIG. 22), suggesting that by organizing themselves into a network, ASCs are able to provide the necessary factors/conditions for their own survival.

V. ASC Blastemas Grown in Suspension Culture Demonstrate the Capacity for Distinct and Dynamic Growth, Morphogenesis, and/or Self-Organization in Response to Various Environmental Conditions.

In order to visualize cell proliferation, cell migration and overall SOM-B topography, in some experiments SOM-Bs were formed with DiI-labeled ASCs. The results demonstrate that SOM-Bs dramatically increased in size when grown in suspension in chemically-defined, growth factor supplemented serum-free or low serum media (AR8). Furthermore, under these serum-free conditions (AR8) SOM-Bs appear to grow primarily in a unidirectional fashion, resulting in an elongated, oval-shape. These results are in contrast to those found when SOM-Bs are grown in DMEM with 10% FBS, which demonstrate a generally spherical growth pattern (see FIGS. 3, 4. 5 and 6).

Figure 4:
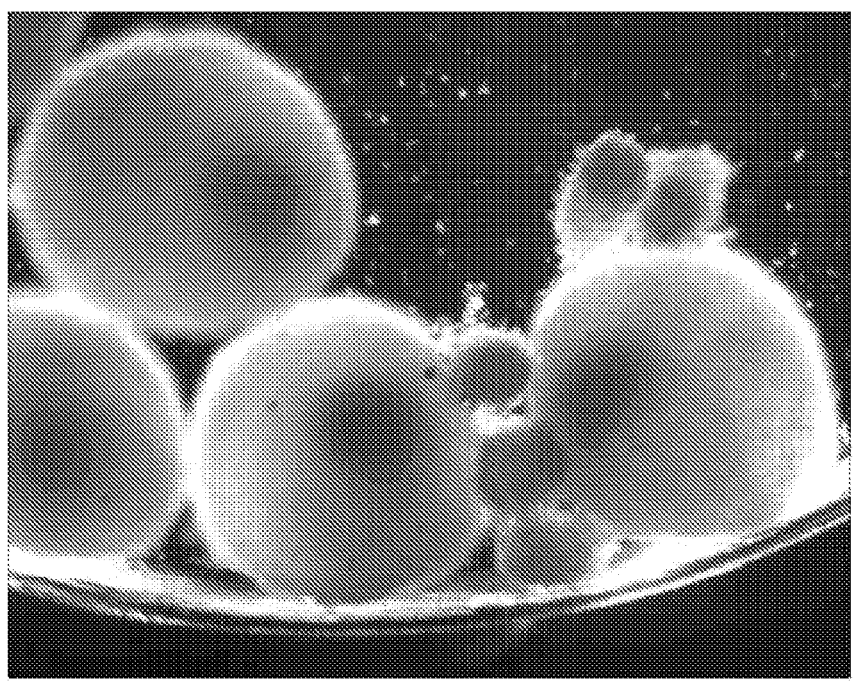
FIG. 4 represents an image of a photomicrograph demonstrating that SOMBs grow up to 10 times their original size after 3-4 weeks in the defined, serum-free medium AR8, while maintaining the "core" of original cells, which is revealed by pre-labeling ASCs with DiI prior to SOMB formation (red, DiI$^+$ "cores" within large spheres that were grown in AR8-0%). Small spheres (red due to DiI) are SOMBs that were kept in DMEM/F12-10% FBS.
Figure 5A:
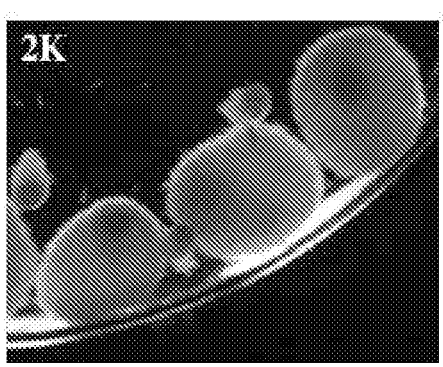
FIGS. 5A-D, represents images of photomicrographs (5A-C) and graphically illustrates SOMB imprint area after 1 month demonstrating that SOM-Bs seem to grow to an optimal size regardless of the original number of cells (2K=2,000 cells).
Figure 5B:
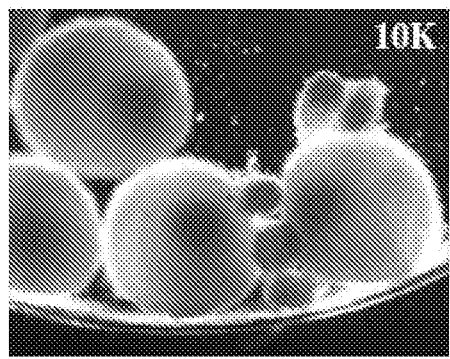
Figure 5C:
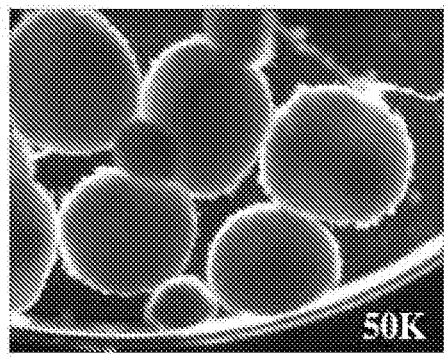
Figure 5D:
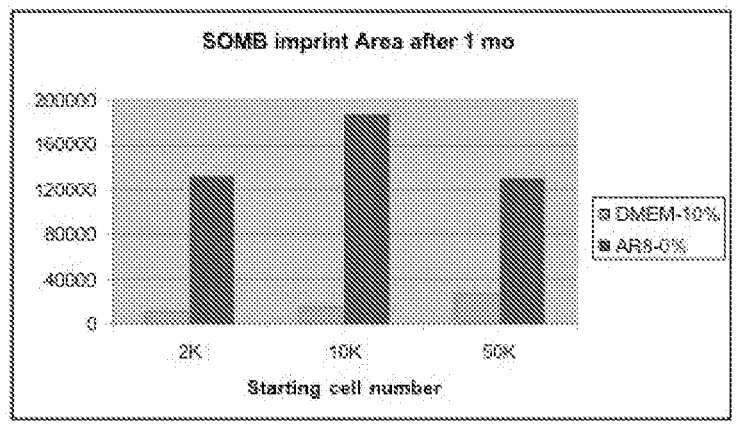
Figure 6:
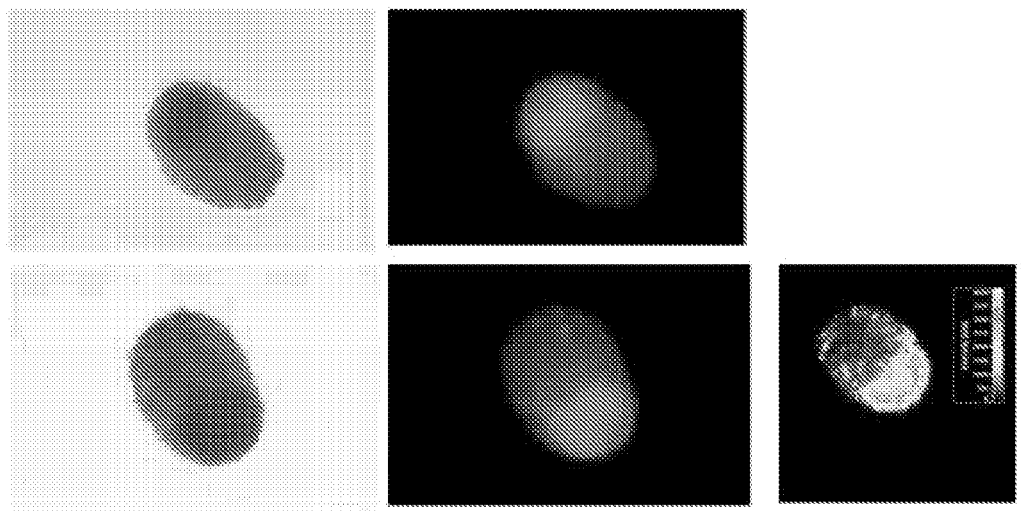
FIG. 6, comprising 5 panels, represents images of photomicrographs demonstrating that DiI pre-labeling of cells prior to SOM-B formation allows for fluorescence-based measurements of polarized growth (lower right panel).
Figure 7:
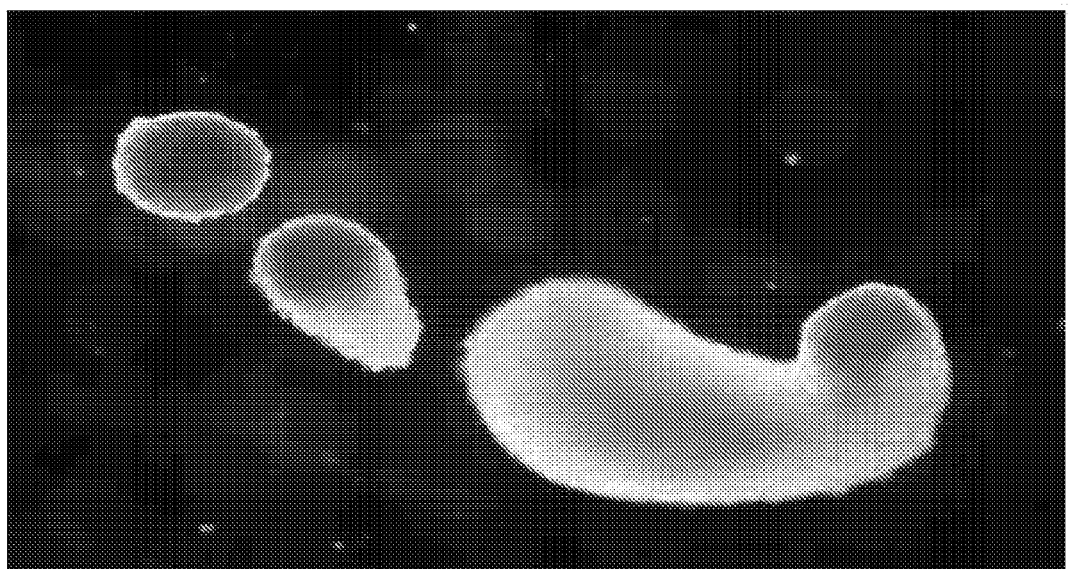
FIG. 7 represents an image of a photomicrograph of a composite figure to demonstrate the progression of SOM-B's polarized growth in AR-type media.
Figure 8A:
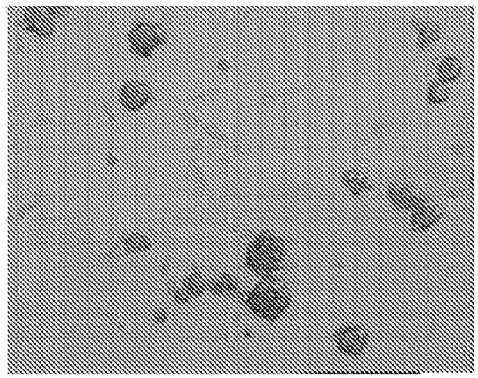
FIG. 8, comprising 4 panels (8A to 8D), represents images of photomicrographs in which ASCs were observed to form SOMBs spontaneously when grown for several passages in zero serum or very low (0.5%) serum conditions.
Figure 8B:
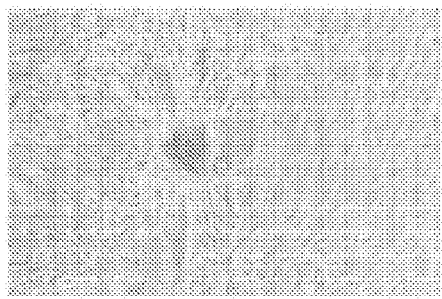
Figure 8C:
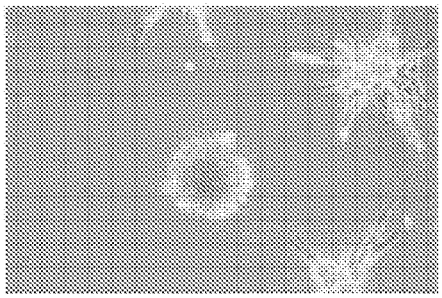
Figure 8D:
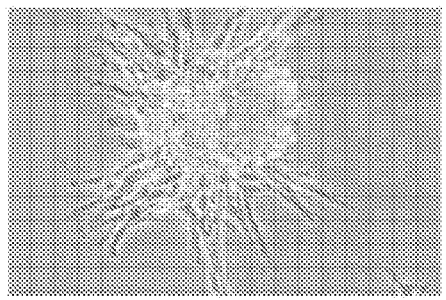

In addition to their striking size increase when grown in AR8 medium, ASC blastemas also display an intriguing polarized topography that is readily reflected by the fluorescent DiI label. As seen in FIGS. 3, 4, 5, 6 and 7, as fluorescently labeled SOM-Bs grow in AR8 medium, the newly formed 'pole' becomes relatively less fluorescent compared to the 'core', or 'pole' of intense fluorescence. This differential growth is quite noticeable, and possibly reflects asymmetric cell division and/or active replication of a specific subpopulation of cells within the SOM-B. Either way, these data strongly support the concept of the SOM-B as a self-regulating stem/stromal cell niche. SOM-Bs grown in 10% FBS not only display less growth, but they also do not demonstrate the striking differential growth that is reflected in a fluorescent gradient (FIGS. 4 and 5).

Figure 12:
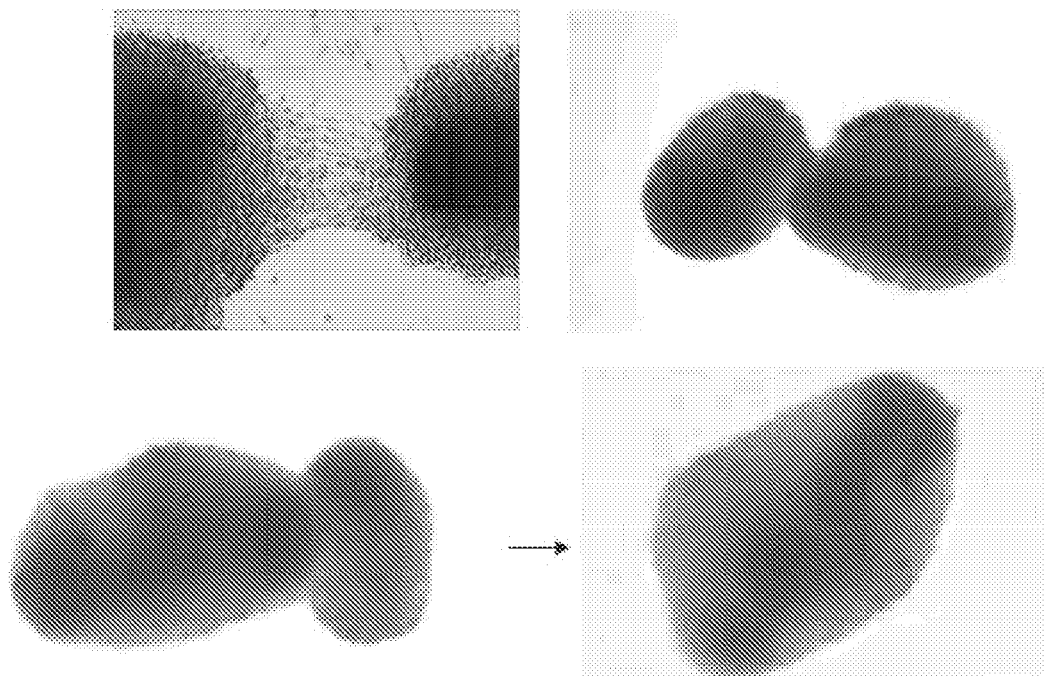
FIG. 12, comprising four panels (12A to 12B), represents images of photomicrographs demonstrating that SOMBs may fuse by extending cell processes into each other when they come into contact.

Additional experiments using BrdU pulsing further demonstrated the directional growth of ASCs within blastemas grown in AR8 medium. It can be seen in the light micrograph of FIG. 19A that SOM-Bs (ASC-MB) grown in suspension culture in serum-free AR8 medium exhibit evidence of polarization and directional growth. H&E histology of the same ASC-MB demonstrates defined nuclei throughout a background of ASC-derived extracellular matrix (19C) A fluorescent micrograph of the same section (19B) demonstrates the more intense, cell and matrix-dense 'core' relative to the growing 'apical' edge (toward the right of the MB). FIG. 19D is a light micrograph of a section from the same ASC-MB that was immunohistochemically stained for BrdU (brown nuclei). The ASC-MB was grown in serum-free medium for 8 days, and pulsed with BrdU for 24 hours prior to fixation and staining. The observed staining pattern correlates perfectly with the proliferative activity observed at the non-fluorescent pole. The ability of ASC blastemas to self-regulate their size and organization is further illustrated by fusion studies. When several polarized blastemas were cultured together in near proximity, they readily adhered to one another. Although initially quite large after fusing, the new SOM-Bs eventually remodel themselves to a size observed for a single SOM-B grown in AR8 medium (up to 500-600 microns in diameter) and which likely reflects apoptosis in the setting of aspect-limit ratios that are defined by effective diffusion distances. Furthermore, the fused SOM-Bs undergo a dynamic reorganization that is evidenced by the alignment and consolidation of fluorescent intense DiI+ 'cores' (FIG. 12). These data support the conclusion that ASC blastemas possess the capacity for distinct and dynamic growth, replication, morphogenesis, and/or self-organization in response to various environmental conditions.

VI. ASC Blastemas in Adherent Culture Demonstrate the Capacity for Multilineage Differentiation.

Adherent ASC blastemas were tested for multilineage developmental plasticity by exposing them to lineage induction conditions soon after adherence. As seen in FIGS. 16-18 and 23-26, ASC blastemas readily undergo adipogenesis and/ or osteogenesis, even after repeated passage (FIGS. 17 and 18) and despite their initial suspension culture in a variety of different medias (FIGS. 23-26).

VII. ASC Blastemas in Suspension Culture Demonstrate the Capacity for Multilineage Differentiation.

Figure 27A:
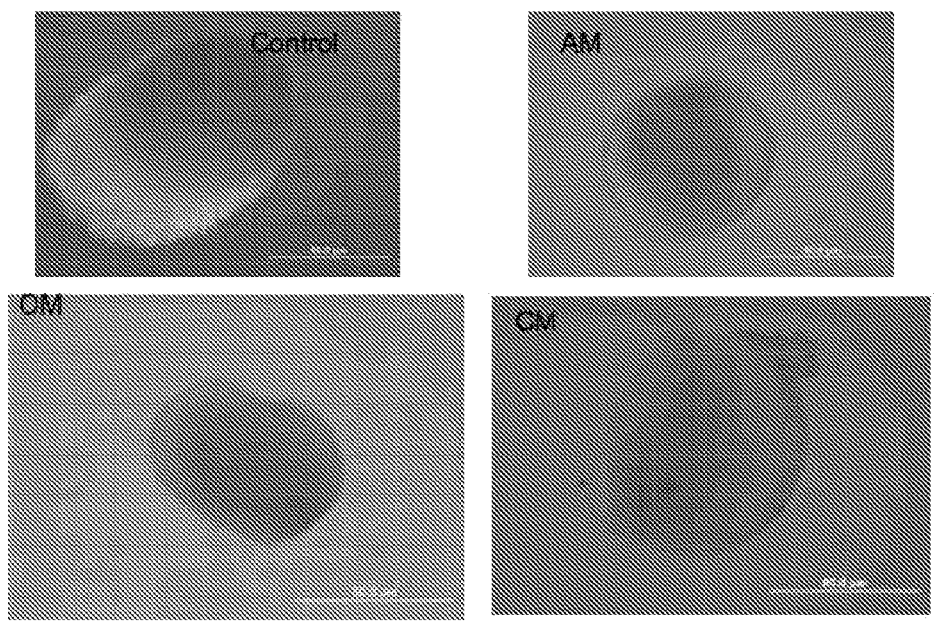
FIGS. 27A and 27B, represents photomicrographic images depicting differentiation of ASC blastemas in suspension culture. ASC blastemas were cultured for two weeks in suspension culture using serum-free AR8 medium. They were then exposed to control medium (AR8 or "Control"), osteogenic medium (OM), or chondrogenic medium (CM) for 3 weeks, and adipogenic medium (AM) for 2 weeks. The blastemas were then frozen, cryosectioned and stained with H and E. The top panel (FIG. 27A), comprising four images, shows blastemas in suspension culture (Control, AM, OM, CM) using light microscopy. The bottom panel, comprising four images (27B), shows the same blastemas as in FIG. 27A after H and E staining.
Figure 27B:
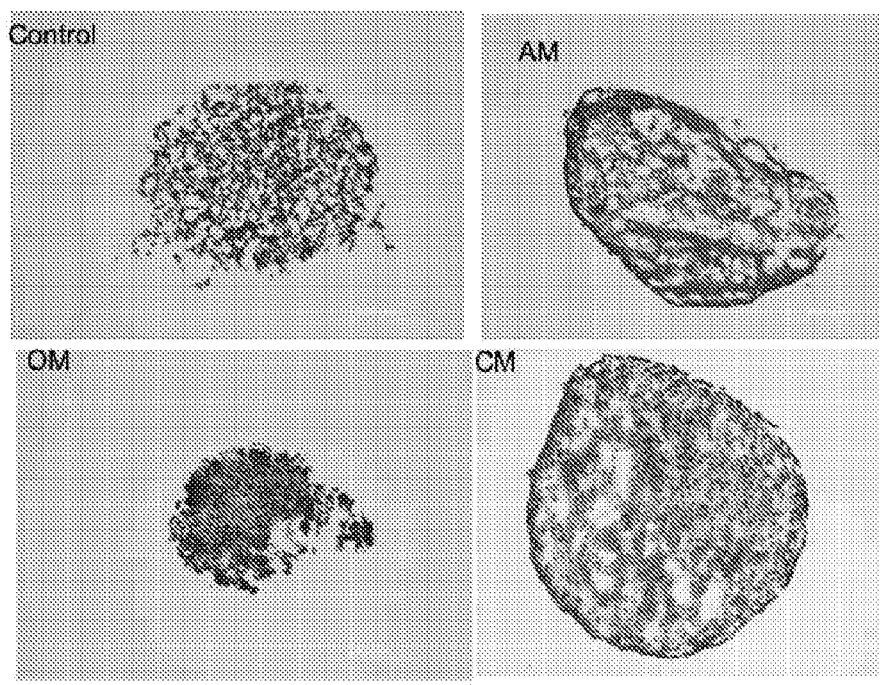
Figure 28:
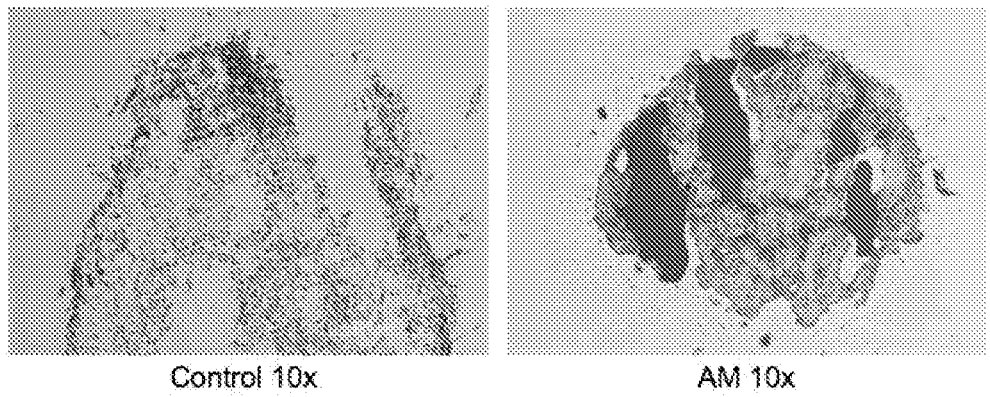
FIG. 28, comprising left (Control) and right (AM at 10× magnification) panels, represents photomicrographic images demonstrating adipogenic differentiation of human ASC blastemas in suspension culture. Human ASC blastema grown in suspension culture in AR8 no serum medium for 2 weeks, then in adipogenic medium (AM) for 6 weeks. Control blastema culture in AR8 no serum medium for 8 weeks. Both blastemas were then cryosectioned and stained for lipid with Oil Red O. Left panel shows blastema in control medium, right panel shows blastema induced with AM exhibited extensive Oil Red O staining. 10× magnification.
Figure 29:
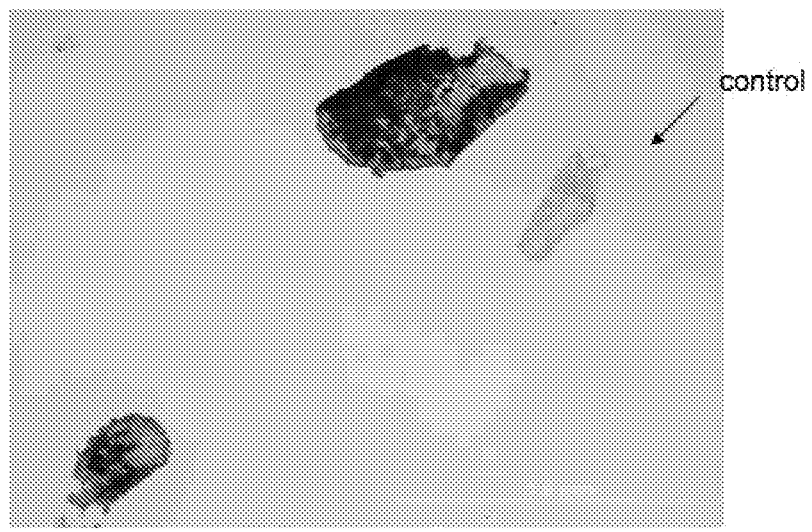
FIG. 29 represents a photomicrographic image demonstrating osteogenic differentiation of human ASC blastemas in suspension culture. Human ASC blastemas were grown in suspension culture in AR8 no serum medium for 2 weeks, then in osteogenic medium (AM) for 6 weeks. Control blastemas (arrow) were cultured in AR8 no serum medium for 8 weeks. Both blastemas were then cryosectioned and stained for calcified matrix using alizarin Red stain. Blastemas grown in OM are readily identified by intense staining, whereas control blastema (arrow) shows no significant staining.

ASC blastemas were tested for multilineage developmental plasticity in suspension culture by exposing them to lineage induction conditions for various lengths of time. As seen in FIGS. 27-29, ASC blastemas in suspension display histologic characteristics suggestive of a capacity for multilineage differentiation.

The disclosures of each and every patent, patent application, and publication cited herein are hereby incorporated by reference herein in their entirety. Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

What is claimed is:

1. A method of culturing adipose tissue-derived stem cells ("ASCs") such that they organize into a three-dimensional multicellular structure;

said method comprising obtaining ASCs;

suspending said ASCs into growth medium, wherein said medium comprises less than about 0.5%-serum;

transferring an aliquot of said growth medium containing ASCs to a solid support having a non-adherent surface to allow said ASCs to aggregate into a three-dimensional multicellular structure; and maintaining said ASCs in a tissue culture environment, thereby forming a three-dimensional multicellular structure, wherein said three-dimensional multicellular structure comprises a self-organizing mesenchymal blastema.

2. The method of claim 1, wherein said aliquot is less than about 100 microliters.

3. The method of claim 2, wherein said aliquot is less than about 30 microliters.

4. The method of claim 1, wherein said three-dimensional multicellular structure is capable of being propagated.

5. The method of claim 1, wherein said ASCs are subjected to at least one purification step prior to being suspended in growth medium.

6. The method of claim 1, wherein said medium is serum-free.

7. The method of claim 1, wherein said ASCs are human ASCs.

8. The method of claim 1, wherein said solid support is a tissue culture plate cover or a bacteriologic plate.

9. The method of claim 1, wherein said ASCs aggregate within about 48 to 72 hours.

10. The method of claim 9, wherein said ASCs aggregate within about 24 hours.

11. The method of claim 1, wherein said self-organizing mesenchymal blastema comprises at least one cell capable of differentiating.

12. The method of claim 11, wherein said at least one cell is capable of differentiating into at least one cell type selected from the group consisting of adipocytes, chondrocytes, and osteoblasts.

13. The method of claim 1, wherein said self-organizing mesenchymal blastema comprises at least one cell capable of proliferating.

14. The method of claim 1, wherein said self-organizing mesenchymal blastema has the ability to migrate.

15. The method of claim 1, wherein said self-organizing mesenchymal blastema has the ability to fuse with at least one other self-organizing mesenchymal blastema.

16. The method of claim 1, wherein the growth medium comprises the basal medium AR8 or AR9.

* * * * *

UNITED STATES PATENT AND TRADEMARK OFFICE
CERTIFICATE OF CORRECTION

PATENT NO. : 8,592,209 B2 Page 1 of 1
APPLICATION NO. : 12/162523
DATED : November 26, 2013
INVENTOR(S) : Khurgel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 792 days.

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,592,209 B2 | Page 1 of 1 |
| APPLICATION NO. | : 12/162523 | |
| DATED | : November 26, 2013 | |
| INVENTOR(S) | : Khurgel et al. | |

It is certified that error appears in the above-identified patent and that said Letters Patent is hereby corrected as shown below:

In the specification

In column 1, lines 8-11, delete "United States Government support under Grant No. HL72141," and insert --government support under HL072141--, therefor.

Signed and Sealed this
Twenty-sixth Day of April, 2016

Michelle K. Lee
*Director of the United States Patent and Trademark Office*